United States Patent
Almansa-Rosales et al.

(10) Patent No.: US 11,111,220 B2
(45) Date of Patent: Sep. 7, 2021

(54) PROPANAMINE DERIVATIVES FOR TREATING PAIN AND PAIN RELATED CONDITIONS

(71) Applicant: ESTEVE PHARMACEUTICALS, S.A., Barcelona (ES)

(72) Inventors: Carmen Almansa-Rosales, Barcelona (ES); Félix Cuevas-Cordobés, Valdemoro (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 16/649,179

(22) PCT Filed: Oct. 16, 2018

(86) PCT No.: PCT/EP2018/078260
§ 371 (c)(1),
(2) Date: Mar. 20, 2020

(87) PCT Pub. No.: WO2019/076904
PCT Pub. Date: Apr. 25, 2019

(65) Prior Publication Data
US 2020/0377464 A1    Dec. 3, 2020

(30) Foreign Application Priority Data
Oct. 16, 2017    (EP) .................................. 17382685

(51) Int. Cl.
| | | |
|---|---|---|
| A61K 31/505 | (2006.01) | |
| C07D 239/48 | (2006.01) | |
| C07C 235/56 | (2006.01) | |
| C07D 211/58 | (2006.01) | |
| C07D 213/75 | (2006.01) | |
| C07D 213/82 | (2006.01) | |
| C07D 239/34 | (2006.01) | |
| C07D 333/20 | (2006.01) | |
| C07D 409/12 | (2006.01) | |
| C07D 413/12 | (2006.01) | |

(52) U.S. Cl.
CPC .......... *C07D 239/48* (2013.01); *C07C 235/56* (2013.01); *C07D 211/58* (2013.01); *C07D 213/75* (2013.01); *C07D 213/82* (2013.01); *C07D 239/34* (2013.01); *C07D 333/20* (2013.01); *C07D 409/12* (2013.01); *C07D 413/12* (2013.01)

(58) Field of Classification Search
None
See application file for complete search history.

(56) References Cited

FOREIGN PATENT DOCUMENTS

| WO | WO2013000651 | 1/2013 |
| WO | WO2014096377 | 6/2014 |
| WO | WO2017191304 | 11/2017 |
| WO | WO2018115064 | 6/2018 |

OTHER PUBLICATIONS

Éliás, Olivér, et al., "Design of novel multiple-acting ligands towards SERT and 5-HT2C receptors", Bioorganic & Medicinal Chemistry Letters, 24, 2014, pp. 2118-2122.
International Search Report for PCT/EP2018/078260 dated Nov. 7, 2016.
Vink, S., et al., "Targeting voltage-gated calcium channels: developments in peptide and small-molecule inhibitors for the treatment of neuropathic pain", British Journal of Pharmacology, 167, 2012, pp. 970-989.
Chabot-Doré, Anne-Julie, et al., "Dual allosteric modulation of opioid antinociceptive potency by α2A-adrenoceptors", Neuropharmacology 99, 2015, pp. 285-300.
Davies, Anthony, et al., "Functional biology of the α2δ subunits of voltage-gated calcium channels", Trends in Pharmacological Sciences, vol. 28, No. 5, 2007, pp. 220-228.
Dolphin, Annette, C., "Calcium channel auxiliary α2δ and β subunits: trafficking and one step beyond", Nature Reviews Neuroscience AOP, Jul. 18, 2012, pp. 542-555.
Dolphin, Annette, C., "The α2δ subunits of voltage-gated calcium channels", Biochimica et Biophysica Acta, 1828, 2013, pp. 1541-1549.
Fairbanks, Carolyn, A., "Pharmacological profiles of Alpha 2 adrenergic receptor agonists identified using genetically altered Mice and isobolographic analysis", Pharmacol. Ther., 123(2), Aug. 2009, pp. 224-238.
Frampton, James, E., "Pregabalin: A review of its use in adults with generalized anxiety disorder", CNS Drugs, 28, 2014, pp. 835-854.
Gilron, Ian, et al., "Combination pharmacotherapy for management of chronic pain: from bench to bedside", Lancet Neurol 12, 2013, pp. 1084-1095.
Goldberg, Daniel, S., et al., "Pain as a global public health priority", BMC Public Health, 11:770, 2011, pp. 1-5.
Hajós, Mihály, et al., "The selective norepinephrine reuptake inhibitor antidepressant reboxetine: pharmacological and clinical profile", CNS Drug Reviews, vol. 10, No. 1, 2004, pp. 23-44.

(Continued)

*Primary Examiner* — Samantha L Shterengarts
(74) *Attorney, Agent, or Firm* — Hueschen and Sage

(57) ABSTRACT

The present invention relates to new compounds of formula (I) that show great affinity and activity towards the subunit α2δ of voltage-gated calcium channels (VGCC), especially the α2δ-1 subunit of voltage-gated calcium channels or dual activity towards the subunit α2δ of voltage-gated calcium channels (VGCC), especially the α2δ-1 subunit of voltage-gated calcium channels, and the noradrenaline transporter (NET). The invention is also related to the process for the preparation of said compounds as well as to compositions comprising them, and to their use as medicaments.

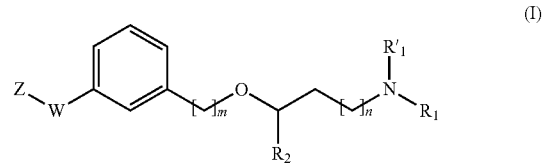

21 Claims, No Drawings

(56) References Cited

OTHER PUBLICATIONS

Hartrick, Crag, T., "Noradrenergic reuptake inhibition in the treatment of pain", Expert Opin. Investig. Drugs, 21(12), 2012, pp. 1827-1834.

Hayashida, Ken-ichiro, et al., "Multiplicative interactions to enhance gabapentin to treat neuropathic pain", European Journal of Pharmacology, 598, 2008, pp. 21-26.

Hopkins, Andrew, L., "Network pharmacology: the next paradigm in drug discovery", Nature Chemical Biology, vol. 4, No. 11, Nov. 2008, pp. 682-690.

Kasper, S., et al., "Reboxetine: the first selective noradrenaline re-uptake inhibitor", Exp. Opin. Pharmacother., 1(4), 2000, pp. 771-782.

Lehàr, Joseph, et al., "Synergistic drug combinatons improve therapeutic selectivity", Nat Biotechnol., 27(7), Jul. 2009, pp. 659-666.

Mason, Stephen, T., "Noradrenaline in the brain: progress in theories of behavioural function", Progress in Neurobiology, vol. 16, 1981, pp. 263-303.

Miranda, Hugo, F., "Isobolographic analysis in mice of the interaction of gabapentin and nortriptyline in relieving orofacial pain", Journal of Orofacial Pain, vol. 27, No. 4, 2013, pp. 361-366.

Miranda, Hugo, F., et al., "Antinociceptive synergism of gabapentin and nortriptyline in mice with partial sciatic nerve ligation", Pharmacology, 95, 2015, pp. 59-64.

Mochizucki, Daisuke, "Serotonin and noradrenaline reuptake inhibitors in animal models of pain", Hum Psychopharmacol Clin Exp, 19, 2004, pp. S15-S19.

Neumaier, Felix, et al., "Voltage-gated calcium channels determinants of channel function and modulation by inorganic cations", Progress in Neurobiology, 129, 2015, pp. 1-36.

Nicolson, Stephen, E., MD, et al., "Comorbid pain, depression, and anxiety: multifaceted pathology allows for multifaceted treatment", Harv Rev Psychiatry, 17, 2009, pp. 407-420.

Ossipov, Michael, H., et al., "Central modulation of pain", J Clin Invest., 120(11), 2010, pp. 3779-3787.

Perret, Danielle, et al., "Targeting voltage-gated calcium channels for neuropathic pain management", Neurotherapeutics: The Journal of the American Society for Experimental NeuroTherapeutics, vol. 6, Oct. 2009, pp. 679-692.

Schröder, W., et al., "Synergistic interaction between the two mechanisms of action of tapentadol in analgesia", The Journal of Pharmacology and Experimental Therapeutics, vol. 337, No. 1, 2011, pp. 312-320.

Tanabe, Mitsuo, et al., "Pain relief by gabapentin and pregabalin via supraspinal mechanisms after peripheral nerve injury", Journal of Neuroscience Research, 86, 2008, pp. 3258-3264.

Turk, Dennis, C., et al., "Treatment of chronic non-cancer pain", Lancet, vol. 377, Jun. 25, 2011, pp. 2226-2235.

Wang, Ruizhong, et al, "Descending facilitation maintains long-term spontaneous neuropathic pain", J Pain., 14(8), Aug. 2013, pp. 845-853.

Zamponi, Gerald, W., et al., "The physiology, pathology, and pharmacology of voltage-gated calcium channels and their future therapeutic potential", Pharmacol Rev, 67, Oct. 2015, pp. 821-870.

Zhang, C., et al., "Synergistic action by multi-targeting compounds produces a potent compound combination for human NSCLC both in vitro and in vivo", Cell Death and Disease, 5, 2014, e1138, pp. 1-12.

PROPANAMINE DERIVATIVES FOR TREATING PAIN AND PAIN RELATED CONDITIONS

FIELD OF THE INVENTION

The present invention relates to new compounds that show great affinity and activity towards the subunit α2δ of voltage-gated calcium channels (VGCC), especially the α2δ-1 subunit of voltage-gated calcium channels or dual activity towards the subunit α2δ of voltage-gated calcium channels (VGCC), especially the α2δ-1 subunit of voltage-gated calcium channels, and the noradrenaline transporter (NET). The invention is also related to the process for the preparation of said compounds as well as to compositions comprising them, and to their use as medicaments.

BACKGROUND OF THE INVENTION

The adequate management of pain represents an important challenge, since currently available treatments provide in many cases only modest improvements, leaving many patients unrelieved (Turk, D. C., Wilson, H. D., Cahana, A.; 2011; Lancet 377; 2226-2235). Pain affects a big portion of the population with an estimated prevalence of 20% and its incidence, particularly in the case of chronic pain, is increasing due to the population ageing. Additionally, pain is clearly correlated to comorbidities, such as depression, anxiety and insomnia, which leads to important productivity losses and socio-economical burden (Goldberg, D. S., McGee, S. J.; 2011; BMC Public Health; 11; 770). Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

Voltage-gated calcium channels (VGCC) are required for many key functions in the body. Different subtypes of voltage-gated calcium channels have been described (Zamponi et al.; Pharmacol. Rev.; 2015; 67; 821-870). The VGCC are assembled through interactions of different subunits, namely α1 ($Ca_v\alpha1$), β ($Ca_v\beta$) α2δ ($Ca_v\alpha2\delta$) and γ ($Ca_v\gamma$). The α1 subunits are the key porous forming units of the channel complex, being responsible for $Ca^{2+}$ conduction and generation of $Ca^{2+}$ influx. The α2δ, β, and γ subunits are auxiliary, although they are very important for the regulation of the channel since they increase the expression of α1 subunits in the plasma membrane as well as modulate their function resulting in functional diversity in different cell types. Based on their physiological and pharmacological properties, VGCC can be subdivided into low voltage-activated T-type ($Ca_v3.1$, $Ca_v3.2$, and $Ca_v3.3$), and high voltage-activated L-($Ca_v1.1$ through $Ca_v1.4$), N—($Ca_v2.2$), P/Q-($Ca_v2.1$), and R—($Ca_v2.3$) types, depending on the channel forming $Ca_v\alpha$ subunits. All of these five subclasses are found in the central and peripheral nervous systems. Regulation of intracellular calcium through activation of these VGCC plays obligatory roles in: 1) neurotransmitter release, 2) membrane depolarization and hyperpolarization, 3) enzyme activation and inactivation, and 4) gene regulation (Perret and Luo; Neurotherapeutics; 2009; 6; 679-692; Zamponi et al., 2015; Neumaier et al.; Prog. Neurobiol.; 2015; 129; 1-36). A large body of data has clearly indicated that VGCC are implicated in mediating various disease states including pain processing. Drugs interacting with the different calcium channel subtypes and subunits have been developed. Current therapeutic agents include drugs targeting L-type $Ca_v1.2$ calcium channels, particularly 1,4-dihydropyridines, which are widely used in the treatment of hypertension. T-type ($Ca_v3$) channels are the target of ethosuximide, widely used in absence epilepsy. Ziconotide, a peptide blocker of N-type ($Ca_v2.2$) calcium channels, has been approved as a treatment of intractable pain.

The $Ca_v1$ and $Ca_v2$ subfamilies contain an auxiliary α2δ subunit which is the therapeutic target of the gabapentinoid drugs of value in certain epilepsies and chronic neuropathic pain (Perret and Luo, 2009; Vink and Alewood; British J. Pharmacol.; 2012; 167; 970-989). To date, there are four known α2δ subunits, each encoded by a unique gene and all possessing splice variants. Each α2δ protein is encoded by a single messenger RNA and is post-translationally cleaved and then linked by disulfide bonds. Four genes encoding α2δ subunits have now been cloned. α2δ-1 was initially cloned from skeletal muscle and shows a fairly ubiquitous distribution. The α2δ-2 and α2δ-3 subunits were subsequently cloned from brain. The most recently identified subunit, α2δ-4, is largely non-neuronal. The human α2δ-4 protein sequence shares 30, 32 and 61% identity with the human α2δ-1, α2δ-2 and α2δ-3 subunits, respectively. The gene structure of all α2δ subunits is similar. All α2δ subunits show several splice variants (Davies et al.; Trends Pharmacol. Sci.; 2007; 28; 220-228; Dolphin, A. C.; Nat. Rev. Neurosci.; 2012; 13; 542-555; Dolphin, A. C.; Biochim. Biophys. Acta; 2013; 1828; 1541-1549).

The $Ca_v\alpha2\delta$-1 subunit may play an important role in neuropathic pain development (Perret and Luo, 2009; Vink and Alewood, 2012). Biochemical data have indicated a significant $Ca_v\alpha2\delta$-1, but not $Ca_v\alpha2\delta$-2, subunit upregulation in the spinal dorsal horn, and DRG (dorsal root ganglia) after nerve injury that correlates with neuropathic pain development. In addition, blocking axonal transport of injury-induced DRG $Ca_v\alpha_2\delta$-1 subunit to the central presynaptic terminals diminishes tactile allodynia in nerve injured animals, suggesting that elevated DRG $Ca_v\alpha2\delta$-1 subunit contributes to neuropathic allodynia.

The $Ca_v\alpha2\delta$-1 subunit (and the $Ca_v\alpha2\delta$-2, but not the $Ca_v\alpha2\delta$-3 and the $Ca_v\alpha2\delta$-4, subunits) is the binding site for gabapentin which has anti-allodynic/hyperalgesic properties in patients and animal models. Because the injury-induced $Ca_v\alpha2\delta$-1 expression correlates with neuropathic pain, development and maintenance, and various calcium channels are known to contribute to spinal synaptic neurotransmission and DRG neuron excitability, the injury-induced $Ca_v\alpha2\delta$-1 subunit upregulation may contribute to the initiation and maintenance of neuropathic pain by altering the properties and/or distribution of VGCC in the subpopulation of DRG neurons and their central terminals, therefore modulating excitability and/or synaptic neuroplasticity in the dorsal horn. Intrathecal antisense oligonucleotides against the $Ca_v\alpha2\delta$-1 subunit can block the nerve injury-induced $Ca_v\alpha2\delta$-1 upregulation and prevent the onset of allodynia and reserve established allodynia.

As above mentioned, the α2δ subunits of VGCC form the binding site for gabapentin and pregabalin which are structural derivatives of the inhibitory neurotransmitter GABA although they do not bind to GABAA, GABAB, or benzodiazepine receptors, or alter GABA regulation in animal brain preparations. The binding of gabapentin and pregabalin to the $Ca_v\alpha2\delta$-1 subunit results in a reduction in the calcium-dependent release of multiple neurotransmitters, leading to efficacy and tolerability for neuropathic pain management. Gabapentinoids may also reduce excitability by inhibiting synaptogenesis (Perret and Luo, 2009; Vink and Alewood, 2012, Zamponi et al., 2015).

Thus, the present invention relates to compounds with inhibitory effect towards the α2δ subunits of voltage-gated calcium channels, preferably towards the α2δ-1 subunit of voltage-gated calcium channels.

It is also known that Noradrenaline (NA), also called norepinephrine, functions in the human brain and body as a hormone and neurotransmitter. Noradrenaline exerts many effects and mediates a number of functions in living organisms. The effects of noradrenaline are mediated by two distinct super-families of receptors, named alpha- and beta-adrenoceptors. They are further divided into subgroups exhibiting specific roles in modulating behavior and cognition of animals. The release of the neurotransmitter noradrenaline throughout the mammalian brain is important for modulating attention, arousal, and cognition during many behaviors (Mason, S. T.; Prog. Neurobiol.; 1981; 16; 263-303).

The noradrenaline transporter (NET, SLC6A2) is a monoamine transporter mostly expressed in the peripheral and central nervous systems. NET recycles primarily NA, but also serotonin and dopamine, from synaptic spaces into presynaptic neurons. NET is a target of drugs treating a variety of mood and behavioral disorders, such as depression, anxiety, and attention-deficit/hyperactivity disorder (ADHD). Many of these drugs inhibit the uptake of NA into the presynaptic cells through NET. These drugs therefore increase the availability of NA for binding to postsynaptic receptors that regulate adrenergic neurotransmission. NET inhibitors can be specific. For example, the ADHD drug atomoxetine is a NA reuptake inhibitor (NRI) that is highly selective for NET. Reboxetine was the first NRI of a new antidepressant class (Kasper et al.; Expert Opin. Pharmacother.; 2000; 1; 771-782). Some NET inhibitors also bind multiple targets, increasing their efficacy as well as their potential patient population.

Endogenous, descending noradrenergic fibers impose analgesic control over spinal afferent circuitry mediating the transmission of pain signals (Ossipov et al.; J. Clin. Invest.; 2010; 120; 3779-3787). Alterations in multiple aspects of noradrenergic pain processing have been reported, especially in neuropathic pain states (Ossipov et a., 2010; Wang et al.; J. Pain; 2013; 14; 845-853). Numerous studies have demonstrated that activation of spinal α2-adrenergic receptors exerts a strong antinociceptive effect. Spinal clonidine blocked thermal and capsaicin-induced pain in healthy human volunteers (Ossipov et a., 2010). Noradrenergic reuptake inhibitors have been used for the treatment of chronic pain for decades: most notably the tricyclic antidepressants, amitriptyline, and nortriptyline. Once released from the presynaptic neuron, NA typically has a short-lived effect, as much of it is rapidly transported back into the nerve terminal. In blocking the reuptake of NA back into the presynaptic neurons, more neurotransmitter remains for a longer period of time and is therefore available for interaction with pre- and postsynaptic $\alpha_2$-adrenergic receptors (AR). Tricyclic antidepressants and other NA reuptake inhibitors enhance the antinociceptive effect of opioids by increasing the availability of spinal NA. The $\alpha_2$A-AR subtype is necessary for spinal adrenergic analgesia and synergy with opioids for most agonist combinations in both animal and humans (Chabot-Doré et al.; Neuropharmacology; 2015; 99; 285-300). A selective upregulation of spinal NET in a rat model of neuropathic pain with concurrent downregulation of serotonin transporters has been shown (Fairbanks et al.; Pharmacol. Ther.; 2009; 123; 224-238). Inhibitors of NA reuptake such as nisoxetine, nortriptyline and maprotiline and dual inhibitors of the noradrenaline and serotonin reuptake such as imipramine and milnacipran produce potent anti-nociceptive effects in the formalin model of tonic pain. Neuropathic pain resulting from the chronic constriction injury of the sciatic nerve was prevented by the dual uptake inhibitor, venlafaxine. In the spinal nerve ligation model, amitriptyline, a non-selective serotonin and noradrenaline reuptake blocker, the preferential noradrenaline reuptake inhibitor, desipramine and the selective serotonin and noradrenaline reuptake inhibitors, milnacipran and duloxetine, produce a decrease in pain sensitivity whereas the selective serotonin reuptake inhibitor, fluoxetine, is ineffective (Mochizucki, D.; Psychopharmacol.; 2004; Supplm. 1; S15-S19; Hartrick, C. T.; Expert Opin. Investig. Drugs; 2012; 21; 1827-1834). A number of nonselective investigational agents focused on noradrenergic mechanisms with the potential for additive or even synergistic interaction between multiple mechanisms of action are being developed (Hartrick, 2012).

Polypharmacology is a phenomenon in which a drug binds multiple rather than a single target with significant affinity. The effect of polypharmacology on therapy can be positive (effective therapy) and/or negative (side effects). Positive and/or negative effects can be caused by binding to the same or different subsets of targets; binding to some targets may have no effect. Multi-component drugs or multi-targeting drugs can overcome toxicity and other side effects associated with high doses of single drugs by countering biological compensation, allowing reduced dosage of each compound or accessing context-specific multitarget mechanisms. Because multitarget mechanisms require their targets to be available for coordinated action, one would expect synergies to occur in a narrower range of cellular phenotypes given differential expression of the drug targets than would the activities of single agents. In fact, it has been experimentally demonstrated that synergistic drug combinations are generally more specific to particular cellular contexts than are single agent activities, such selectivity is achieved through differential expression of the drugs' targets in cell types associated with therapeutic, but not toxic, effects (Lehar et al.; Nat. Biotechnol.; 2009; 27; 659-666).

In the case of chronic pain, which is a multifactorial disease, multi-targeting drugs may produce concerted pharmacological intervention of multiple targets and signaling pathways that drive pain. Because they actually make use of biological complexity, multi-targeting (or multi-component drugs) approaches are among the most promising avenues toward treating multifactorial diseases such as pain (Gilron et al.; Lancet Neurol.; 2013; 12(11); 1084-1095). In fact, positive synergistic interaction for several compounds, including analgesics, has been described (Schröder et al; J. Pharmacol. Exp. Ther.; 2011; 337; 312-320; Zhang et al.; Cell Death Dis.; 2014; 5; e1138; Gilron et al., 2013).

Given the significant differences in pharmacokinetics, metabolisms and bioavailability, reformulation of drug combinations (multi-component drugs) is challenging. Further, two drugs that are generally safe when dosed individually cannot be assumed to be safe in combination. In addition to the possibility of adverse drug-drug interactions, if the theory of network pharmacology indicates that an effect on phenotype may derive from hitting multiple targets, then that combined phenotypic perturbation may be efficacious or deleterious. The major challenge to both drug combination strategies is the regulatory requirement for each individual drug to be shown to be safe as an individual agent and in combination (Hopkins, A. L.; Nat. Chem. Biol.; 2008; 4; 682-690).

An alternative strategy for multitarget therapy is to design a single compound with selective polypharmacology (multi-targeting drug). It has been shown that many approved drugs act on multiple targets. Dosing with a single compound may have advantages over a drug combination in terms of equitable pharmacokinetics and biodistribution. Indeed, troughs in drug exposure due to incompatible pharmacokinetics between components of a combination therapy may create a low-dose window of opportunity where a reduced selection pressure can lead to drug resistance. In terms of drug registration, approval of a single compound acting on multiple targets faces significantly lower regulatory barriers than approval of a combination of new drugs (Hopkins, 2008).

Thus, in a preferred embodiment, the compounds of the present invention having affinity for the α2δ subunits of voltage-gated calcium channels, preferably towards the α2δ-1 subunit of voltage-gated calcium channels, additionally have inhibitory effect towards noradrenaline transporter (NET) and are, thus, more effective to treat chronic pain.

There are two potentially important interactions between the NET and the α2δ-1 inhibition: 1) synergism in analgesia, thus reducing the risk of specific side effects; and 2) inhibition of pain-related affective comorbidities such as anxiety and/or depressive-like behaviors (Nicolson et al.; Harv. Rev. Psychiatry; 2009; 17; 407-420).

1) Preclinical research has demonstrated that gabapentinoids attenuated pain-related behaviors through supraspinal activation of the descending noradrenergic system (Tanabe et al.; J. Neuroosci. Res.; 2008; Hayashida, K.; Eur. J. Pharmacol.; 2008; 598; 21-26). In consequence, the α2δ-1-related analgesia mediated by the NA-induced activation of spinal α$_2$-adrenergic receptors can be potentiated by the inhibition of the NET. Some evidence from combination studies in preclinical models of neuropathic pain exist. Oral duloxetine with gabapentin was additive to reduce hypersensitivity induced by nerve injury in rats (Hayashida; 2008). The combination of gabapentin and nortriptyline drugs was synergic in mice submitted to orofacial pain and to peripheral nerve injury model (Miranda, H. F. et al.; J. Orofac. Pain; 2013; 27; 361-366; Pharmacology; 2015; 95; 59-64).

2) Drug modulation of the NET and the α2δ-1 has been shown to produce antidepressant and anti-anxiety effects respectively (Frampton, J. E.; CNS Drugs; 2014; 28; 835-854; Hajós, M. et al.; CNS Drug Rev.; 2004; 10; 23-44). In consequence, a dual drug that inhibited the NET and the α2δ-1 subunit of VGCC may also stabilize pain-related mood impairments by acting directly on both physical pain and the possible mood alterations.

SUMMARY OF THE INVENTION

The present invention discloses novel compounds with great affinity to the α2δ subunit of voltage-gated calcium channels, more specifically to the α2δ-1 subunit, and which in preferred embodiments also have inhibitory effect towards the noradrenaline transporter (NET), thus resulting in a dual activity for treating pain and pain related disorders.

The main object of the present invention is related to compounds of general formula (I):

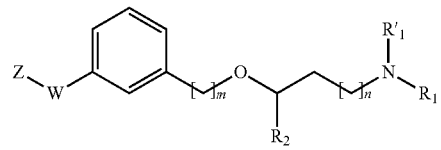

wherein:
$R_1$ and $R'_1$ are independently selected from a hydrogen atom and a branched or unbranched $C_{1-6}$ alkyl radical;

$R_2$ is a 6-membered aryl radical optionally substituted by a halogen atom, a branched or unbranched $C_{1-6}$-alkyl radical, a branched or unbranched $C_{1-6}$-alkoxy radical, a $C_{1-6}$-haloalcoxy radical, a $C_{1-6}$-haloalkyl radical or a hydroxyl radical; or a substituted or unsubstituted 5 or 6-membered heteroaryl radical having at least one heteroatom selected from N, O and S;

n is 1;
m is 0 or 1;
W is —$(CH_2)_p$—; —C(O)—; or a bond;
p is 1 or 2;
Z is $NR_3R_4$;
$R_3$ is a hydrogen atom; a branched or unbranched $C_{1-6}$ alkyl radical; a benzyl radical; or a phenyl radical;
$R_4$ is a branched or unbranched $C_{1-6}$ alkyl radical, optionally substituted by a halogen atom, a hydroxyl radical, a branched or unbranched $C_{1-6}$ alcoxy radical, or a —$NR_{4a}R_{4b}$ radical; a —$(CH_2)_s$-heteroaryl radical where the heteroaryl group is a 5 or 6-membered ring with at least one nitrogen atom as heteroatom, optionally substituted by a —$NR_{4c}R_{4d}$ radical and s being 0, 1 or 2; a heterocycloalkyl radical optionally substituted by $R_{4e}$; a —$(CH_2)_r$-aryl radical where the aryl group is a 6-membered ring, optionally substituted by at least one $R_5$ radical and r being 0, 1 or 2; or a —$C(O)R_6$ radical;

$R_{4a}$, $R_{4b}$, $R_{4c}$, $R_{4d}$ and $R_{4e}$ are independently selected from hydrogen atom and a branched or unbranched $C_{1-6}$ alkyl radical;

$R_5$ is a hydrogen atom; a hydroxyl radical; a branched or unbranched $C_{1-6}$-alkoxy radical; a —$(CH_2)_j$—$NR_{5a}R_{5b}$ radical; a —$NR_{5c}R_{5d}$ radical; or a 5-membered heteroaromatic ring containing one or more N and/or O as heteroatoms, optionally substituted by $R_{5e}$;

$R_{5a}$, $R_{5b}$, $R_{5c}$, $R_{5d}$ and $R_{5e}$ are independently a hydrogen atom or a branched or unbranched $C_{1-6}$ alkyl radical;

j is 0 or 1;
$R_6$ is a branched or unbranched $C_{1-6}$ alkyl radical; a —$(CH_2)_q$—$NR_{6a}R_{6b}$ radical; or a 5 or 6-membered nitrogen containing heteroaryl ring optionally containing at least one additional heteroatom selected from O and N and optionally substituted by at least one $R_7$; or a 6-membered aryl ring optionally substituted by at least one $R_8$;

$R_{6a}$ and $R_{6b}$ are independently selected from hydrogen atom and a branched or unbranched $C_{1-6}$ alkyl radical;

q is 0, 1, 2, 3 or 4;
$R_7$ is selected from an hydrogen atom, a branched or unbranched $C_{1-6}$-alkoxy radical, a branched or unbranched $C_{1-6}$-alkylthio radical; a —$NR_{7a}R_{7b}$ radical; and a substituted or unsubstituted 5-membered heterocycloalkyl ring with at least one heteroatom selected from O, N and S;

$R_{7a}$ and $R_{7b}$ are independently selected from a hydrogen atom and a branched or unbranched $C_{1-6}$alkyl radical;

$R_8$ is a hydrogen atom, a halogen atom, a branched or unbranched $C_{1-6}$-alkyl radical or a —$(CH_2)_t$—$NR_{8a}R_{8b}$ radical;

t is 0 or 1;
$R_{8a}$ and $R_{8b}$ are independently selected from hydrogen atom and a branched or unbranched $C_{1-6}$ alkyl radical;

or a pharmaceutically acceptable salt, isomer, prodrug or solvate thereof.

It is also an object of the invention different processes for the preparation of compounds of formula (I).

Another object of the invention refers to the use of such compounds of general formula (I) for the treatment and/or prophylaxis of the α2δ-1 subunit mediated disorders and more preferably for the treatment and/or prophylaxis of disorders mediated by the α2δ-1 subunit of voltage-gated calcium channels and/or the noradrenaline transporter (NET). The compounds of the present invention are particularly suited for the treatment of pain, specially neuropathic pain, and pain related or pain derived conditions.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to compounds of general formula (I)

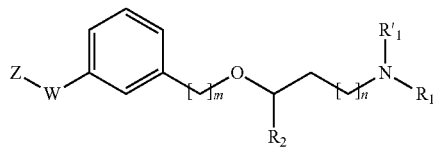

(I)

wherein:

$R_1$ and $R'_1$ are independently selected from hydrogen atom and a branched or unbranched $C_{1-6}$ alkyl radical;

$R_2$ is a 6-membered aryl radical optionally substituted by a halogen atom, a branched or unbranched $C_{1-6}$-alkyl radical, a branched or unbranched $C_{1-6}$-alkoxy radical, a $C_{1-6}$-haloalcoxy radical, a $C_{1-6}$-haloalkyl radical or a hydroxyl radical; or a substituted or unsubstituted 5 or 6-membered heteroaryl radical having at least one heteroatom selected from N, O and S;

n is 1;

m is 0 or 1;

W is —$(CH_2)_p$—; —C(O)—; or a bond;

p is 1 or 2;

Z is $NR_3R_4$;

$R_3$ is a hydrogen atom; a branched or unbranched $C_{1-6}$ alkyl radical; a benzyl radical; or a phenyl radical;

$R_4$ is a branched or unbranched $C_{1-6}$ alkyl radical, optionally substituted by a halogen atom, a hydroxyl radical, a branched or unbranched $C_{1-6}$ alcoxy radical, or a —$NR_{4a}R_{4b}$ radical; a —$(CH_2)_s$-heteroaryl radical where the heteroaryl group is a 5 or 6-membered ring with at least one nitrogen atom as heteroatom, optionally substituted by a —$NR_{4c}R_{4d}$ radical and s being 0, 1 or 2; a heterocycloalkyl radical optionally substituted by $R_{4e}$; a —$(CH_2)_r$-aryl radical where the aryl group is a 6-membered ring, optionally substituted by at least one $R_5$ radical and r being 0, 1 or 2; or a —C(O)$R_6$ radical;

$R_{4a}$, $R_{4b}$, $R_{4c}$, $R_{4d}$ and $R_{4e}$ are independently selected from a hydrogen atom and a branched or unbranched $C_{1-6}$ alkyl radical;

$R_5$ is a hydrogen atom; a hydoxy radical; a branched or unbranched $C_{1-6}$-alkoxy radical; a —$(CH_2)_j$—$NR_{5a}R_{5b}$ radical; a —$NR_{5c}R_{5d}$ radical; or a 5-membered heteroaromatic ring containing one or more N and/or O as heteroatoms, optionally substituted by $R_{5e}$;

$R_{5a}$, $R_{5b}$, $R_{5c}$, $R_{5d}$ and $R_{5e}$ are independently a hydrogen atom or a branched or unbranched $C_{1-6}$ alkyl radical;

j is 0 or 1;

$R_6$ is a branched or unbranched $C_{1-6}$ alkyl radical; a —$(CH_2)_q$—$NR_{6a}R_{6b}$ radical; or a 5 or 6-membered nitrogen containing heteroaryl ring optionally containing at least one additional heteroatom selected from O and N and optionally substituted by at least one $R_7$; or a 6-membered aryl ring optionally substituted by at least one $R_8$;

$R_{6a}$ and $R_{6b}$ are independently selected from a hydrogen atom and a branched or unbranched $C_{1-6}$ alkyl radical;

q is 0, 1, 2, 3 or 4;

$R_7$ is selected from a hydrogen atom, a branched or unbranched $C_{1-6}$-alkoxy radical, a branched or unbranched $C_{1-6}$-alkylthio radical; a —$NR_{7a}R_{7b}$ radical; and a substituted or unsubstituted 5-membered heterocycloalkyl ring with at least one heteroatom selected from O, N and S;

$R_{7a}$ and $R_{7b}$ are independently selected from a hydrogen atom and a branched or unbrached $C_{1-6}$-alkyl radical;

$R_8$ is a hydrogen atom, a halogen atom, a branched or unbranched $C_{1-6}$-alkyl radical or a —$(CH_2)_t$—$NR_{8a}R_{8b}$ radical;

t is 0 or 1;

$R_{8a}$ and $R_{8b}$ are independently selected from a hydrogen atom and a branched or unbranched $C_{1-6}$-alkyl radical;

or a pharmaceutically acceptable salt, isomer, prodrug or solvate thereof.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

Any compound referred to herein is intended to represent such specific compound as well as certain variations or forms. In particular, compounds referred to herein may have asymmetric centers and therefore may exist in different enantiomeric or diastereomeric forms. Thus, any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same as, or different to, the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

"Halogen" or "halo" as referred in the present invention represent fluorine, chlorine, bromine or iodine. When the term "halo" is combined with other substituents, such as for instance "$C_{1-6}$ haloalkyl" or "$C_{1-6}$ haloalkoxy" it means that the alkyl or alkoxy radical can respectively contain at least one halogen atom.

A "leaving group" is a group that in a heterolytic bond cleavage keeps the electron pair of the bond. Suitable leaving groups are well known in the art and include Cl, Br, I and —O—SO$_2$R$^{14}$, wherein R$^{14}$ is F, $C_{1-4}$-alkyl, $C_{1-4}$-haloalkyl, or optionally substituted phenyl. The preferred leaving groups are Cl, Br, I, tosylate, mesylate, triflate, nonaflate and fluorosulphonate.

"$C_{1-6}$ alkyl", as referred to in the present invention, are saturated aliphatic radicals. They may be linear (unbranched) or branched and are optionally substituted. $C_{1-6}$-alkyl as expressed in the present invention means an alkyl radical of 1, 2, 3, 4, 5 or 6 carbon atoms. Preferred alkyl radicals according to the present invention include but are not restricted to methyl, ethyl, propyl, n-propyl, isopropyl, butyl, n-butyl, tert-butyl, isobutyl, sec-butyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl. The most preferred alkyl radical are $C_{1-4}$ alkyl, such as methyl, ethyl, propyl, n-propyl, isopropyl, butyl, n-butyl, tert-butyl, isobutyl, sec-butyl, 1-methylpropyl, 2-methylpropyl or 1,1-dimethylethyl. Alkyl radicals, as defined in the present invention, may be optionally mono- or polysubstituted by substituents independently selected from a halogen atom, a $C_{1-6}$-alkoxy radical, a $C_{1-6}$-alkyl radical, a $C_{1-6}$-haloalcoxy radical, a $C_{1-6}$-haloalkyl radical, a trihaloalkyl radical, a hydroxyl radical and an amino radical such as a —NR$_{4a}$R$_{4b}$ radical.

"$C_{1-6}$ alkoxy" as referered to in the present invention, is understood as meaning an alkyl radical as defined above attached via oxygen linkage to the rest of the molecule. Examples of alkoxy include, but are not limited to methoxy, ethoxy, propoxy, butoxy or tert-butoxy.

"Heterocycloalkyl" as referred to in the present invention, are understood as meaning saturated and unsaturated (but not aromatic), generally 5 or 6 membered cyclic hydrocarbons which can optionally be unsubstituted, mono- or polysubstituted and which have at least one heteroatom in their structure selected from N, O and S. Examples for heterocycloalkyl radical preferably include but are not restricted to pyrroline, pyrrolidine, pyrazoline, aziridine, azetidine, tetrahydropyrrole, oxirane, oxetane, dioxetane, tetrahydropyrane, tetrahydrofurane, dioxane, dioxolane, oxazolidine, piperidine, piperazine, morpholine, azepane or diazepane. Heterocycloalkyl radicals, as defined in the present invention, may be optionally mono- or polysubstituted by substitutents independently selected from a halogen atom, a $C_{1-6}$-alkyl radical, a $C_{1-6}$-alkoxy radical, a $C_{1-6}$-haloalkoxy radical, a $C_{1-6}$-haloalkyl radical, a trihaloalkyl radical and a hydroxyl radical. More preferably heterocycloalkyl in the context of the present invention are 5 or 6-membered ring systems optionally at least monosubstituted.

"Aryl" as referred to in the present invention, is understood as meaning ring systems with at least one aromatic ring but without heteroatoms even in only one of the rings. These aryl radicals may optionally be mono- or polysubstituted by substitutents independently selected from a halogen atom, a branched or unbranched $C_{1-6}$-alkyl radical, a branched or unbranched $C_{1-6}$-alkoxy radical, a $C_{1-6}$-haloalcoxy radical, a $C_{1-6}$-haloalkyl radical and a hydroxyl radical. Preferred examples of aryl radicals include but are not restricted to phenyl, naphthyl, fluoranthenyl, fluorenyl, tetralinyl, indanyl or anthracenyl radicals, which may optionally be mono- or polysubstituted, if not defined otherwise. More preferably aryl in the context of the present invention is a 6-membered ring system optionally at least monosubstituted.

"Heteroaryl" as referred to in the present invention, is understood as meaning heterocyclic ring systems which have at least one aromatic ring and may optionally contain one or more heteroatoms from the group consisting of N, O and S and may optionally be mono- or polysubstituted by substituents independently selected from a halogen atom, a $C_{1-6}$-alkyl radical, a $C_{1-6}$-alkoxy radical, a $C_{1-6}$-haloalkoxy radical, a $C_{1-6}$-haloalkyl radical, a trihaloalkyl radical and a hydroxyl radical. Preferred examples of heteroaryls include but are not restricted to furan, benzofuran, pyrrole, pyridine, pyrimidine, pyridazine, pyrazine, thiophene, quinoline, isoquinoline, phthalazine, triazole, pyrazole, isoxazole, indole, benzotriazole, benzodioxolane, benzodioxane, benzimidazole, carbazole and quinazoline. More preferably heteroaryl in the context of the present invention are 5 or 6-membered ring systems optionally at least monosubstituted.

"Heterocyclic ring" or "heterocyclic system", as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O. Preferred substituents for heterocyclyl radicals, according to the present invention, are F, Cl, Br, I, NH$_2$, SH, OH, SO$_2$, CF$_3$, carboxy, amido, cyano, carbamyl, nitro, phenyl, benzyl, —SO$_2$NH$_2$, $C_{1-6}$ alkyl and/ or $C_{1-6}$-alkoxy.

The term "ring system" according to the present invention refers to a system consisting of at least one ring of connected atoms but including also systems in which two or more rings of connected atoms are joined with "joined" meaning that the respective rings are sharing one (like a spiro structure), two or more atoms being a member or members of both joined rings. The "ring system" thus defined comprises saturated, unsaturated or aromatic carbocyclic rings which contain optionally at least one heteroatom as ring member and which are optionally at least mono-substituted and may be joined to other carbocyclic ring systems such as aryl radicals, heteroaryl radicals, cycloalkyl radicals etc.

The terms "condensed", "annulated" or "annelated" are also used by those skilled in the art to designate this kind of join.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition particularly includes physiologically acceptable salts, this term must be understood as equivalent to "pharmacologically acceptable salts".

The term "pharmaceutically acceptable salts" in the context of this invention means any salt that is tolerated physiologically (normally meaning that it is not toxic, particularly as a result of the counter-ion) when used in an appropriate manner for a treatment, particularly applied or used in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" is to be understood as meaning any form of the active compound according to the invention in which this compound has attached to it via non-covalent binding another molecule (most likely a polar solvent) especially including hydrates and alcoholates, e.g. methanolate.

The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the compounds of the invention: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (april 2002).

Any compound that is a prodrug of a compound of formula (I) is within the scope of the invention. Particularly favored prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

In a particular and preferred embodiment of the invention, $R_2$ is a phenyl radical optionally substituted by a halogen atom, a branched or unbranched $C_{1-6}$-alkyl radical, a branched or unbranched $C_{1-6}$-alkoxy radical, a $C_{1-6}$-haloalkoxy radical, a $C_{1-6}$-haloalkyl radical or a hydroxyl radical; or a substituted or unsubstituted tiophene radical. More preferably, the phenyl radical and the tiophene radical are unsubstituted.

In another particular and preferred embodiment of the invention, $R_4$ is:
 a $C_{1-6}$ alkyl radical, preferably methyl or ethyl, optionally substituted by a —$NR_{4a}R_{4b}$ radical;
 a group selected from:

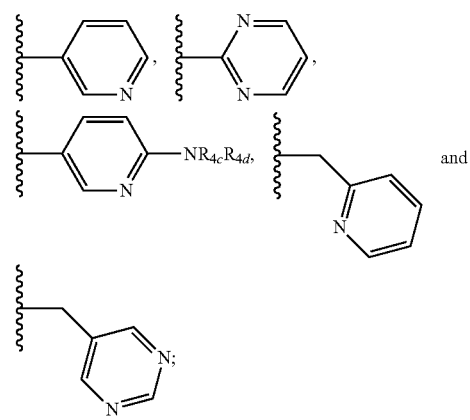

a radical:

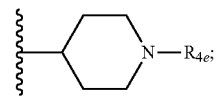

a radical selected from:

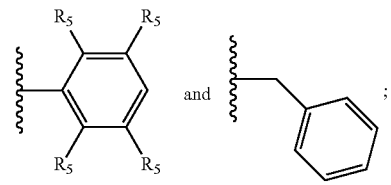

or
 a —$C(O)R_6$ radical;
 wherein $R_{4a}$, $R_{4b}$, $R_{4c}$, $R_{4d}$, $R_{4e}$, $R_5$ and $R_6$ are as defined before.

In a still particular embodiment of the invention, $R_5$ is independently selected from a hydrogen atom; a branched or unbranched $C_{1-6}$ alkoxy radical; a —$(CH_2)_j$—$NR_{5a}R_{5b}$ radical, a —$NR_{5c}R_{5d}$ radical and the radical:

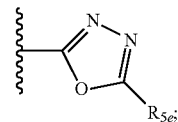

wherein $R_{5a}$, $R_{5b}$, $R_{5c}$, $R_{5d}$, $R_{5e}$ and j are as defined before.

Another particular embodiment of the invention is that where $R_6$ is selected from a branched or unbranched $C_{1-6}$ alkyl radical, preferably methyl, ethyl or propyl; a —$(CH_2)_q$—$NR_{6a}R_{6b}$ radical and a radical selected from:

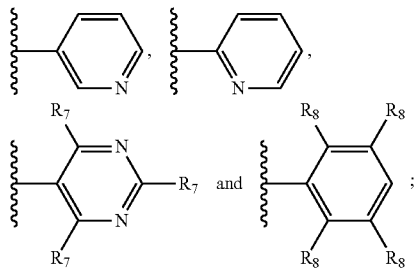

wherein $R_{6a}$, $R_{6b}$, $R_7$, $R_8$ and q are as defined before.

Yet another particular embodiment is that in which $R_7$ is a hydrogen atom, a methoxy radical; a methylthio radical, a —$NR_{7a}R_{7b}$ radical or the following radical:

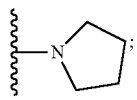

wherein $R_{7a}$ and $R_{7b}$ are as defined before.

Another particular embodiment of the invention contemplates that $R_8$ is a hydrogen atom, a halogen atom, preferably a F, Cl or Br; or a —$(CH_2)_t$—$NR_{8a}R_{8b}$ radical where $R_{8a}$, $R_{8b}$ and t are as defined above.

A particularly preferred embodiment of the invention is represented by compounds of general formula (I) where $R_1$ and $R'_1$ are independently selected from a hydrogen atom and a branched or unbranched $C_{1-6}$ alkyl radical;

$R_2$ is a phenyl radical optionally substituted by halogen atom, a branched or unbranched $C_{1-6}$-alkyl radical, a branched or unbranched $C_{1-6}$-alkoxy radical, a $C_{1-6}$-haloalkoxy radical, a $C_{1-6}$-haloalkyl radical or a hydroxyl radical; or a substituted or unsubstituted tiophene radical;

n is 1;

m is 0 or 1;

W is —$(CH_2)_p$—; —$C(O)$—; or a bond;

p is 1 or 2;

Z is $NR_3R_4$;

$R_3$ is a hydrogen atom; a branched or unbranched $C_{1-6}$ alkyl radical; a benzyl radical; or a phenyl radical; and $R_4$ is:

a branched or unbranched $C_{1-6}$ alkyl radical, preferably methyl or ethyl, optionally substituted by a —$NR_{4a}R_{4b}$ radical;

a radical selected from:

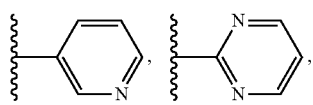

-continued

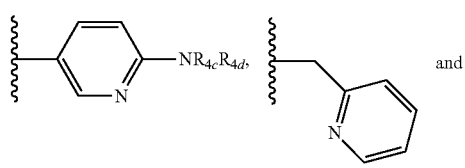

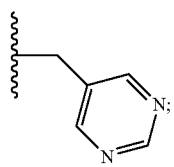

a radical:

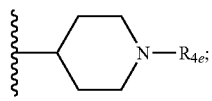

a radical selected from:

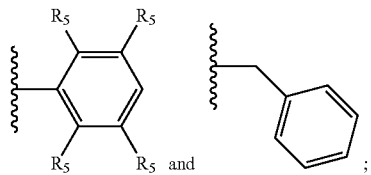

or a —$C(O)R_6$ radical;

$R_{4a}$, $R_{4b}$, $R_{4c}$, $R_{4d}$ and $R_{4e}$ are independently selected from a hydrogen atom and a branched or unbranched $C_{1-6}$ alkyl radical;

$R_5$ is independently selected from a hydrogen atom; a branched or unbranched $C_{1-6}$ alkoxy radical; a —$(CH_2)_j$—$NR_{5a}R_{5b}$ radical, a —$NR_{5c}R_{5d}$ radical and the group:

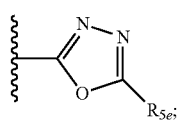

$R_{5a}$, $R_{5b}$, $R_{5c}$, $R_{5d}$ and $R_{5e}$ are independently a hydrogen atom or a branched or unbranched $C_{1-6}$ alkyl radical;

j is 0 or 1;

$R_6$ is selected from a branched or unbranched $C_{1-6}$ alkyl radical, preferably methyl, ethyl or propyl; a —$(CH_2)_q$—$NR_{6a}R_{6b}$ radical and a group selected from:

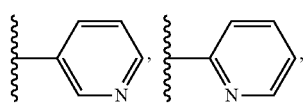

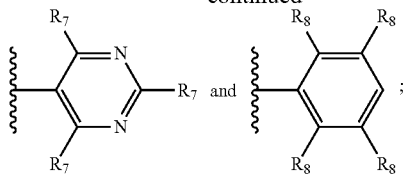

$R_{6a}$ and $R_{6b}$ are independently selected from H and $C_{1-6}$ alkyl;

q is 0, 1, 2, 3 or 4;

$R_7$ is selected from an hydrogen atom, a methoxy radical; a methylthio radical, a —$NR_{7a}R_{7b}$ radical and the following group:

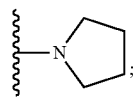

$R_{7a}$ and $R_{7b}$ are independently selected from a H and a $C_{1-6}$alkyl radical;

$R_8$ is hydrogen atom, a halogen atom, preferably a F, Cl or Br; or a —$(CH_2)_t$—$NR_{8a}R_{8b}$ radical;

t is 0 or 1;

$R_{8a}$ and $R_{8b}$ are independently selected from H and $C_{1-6}$ alkyl;

or a pharmaceutically acceptable salt, isomer, prodrug or solvate thereof.

Another particularly preferred embodiment of the invention is represented by compounds of formula (I) having the following subformulas ($I_{1a}$), ($I_{1b}$), ($I_{2a}$), ($I_{2b}$), ($I_{2c}$) or ($I_{2ca}$):

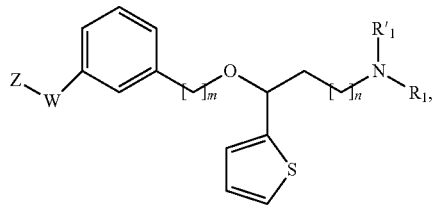
($I_{1a}$)

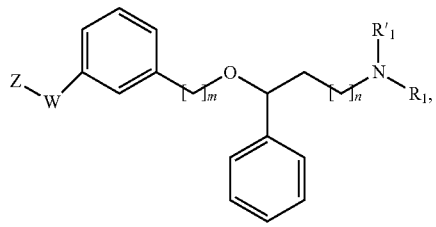
($I_{1b}$)

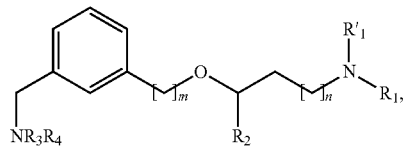
($I_{2a}$)

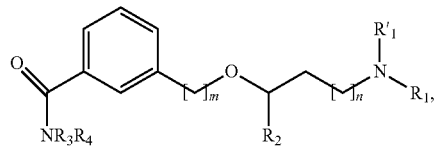
($I_{2b}$)

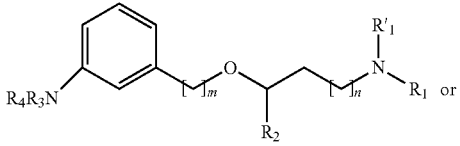
($I_{2c}$)

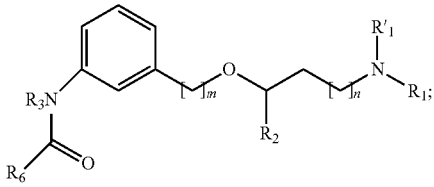
($I_{2ca}$)

wherein $R_1$, $R'_1$, $R_2$, $R_3$, $R_4$, $R_6$, W, Z, m and n are as defined above;

or a pharmaceutically acceptable salt, isomer, prodrug or solvate thereof.

The compounds of the present invention represented by the above described formula (I), ($I_{1a}$), ($I_{1b}$), ($I_{2a}$), ($I_{2b}$), ($I_{2c}$) or ($I_{2ca}$) may include enantiomers depending on the presence of chiral centers or isomers depending on the presence of double bonds (e.g. Z, E). The single isomers, enantiomers or diastereoisomers and mixtures thereof fall within the scope of the present invention.

Among all the compounds described in the general formula (I), the following compounds are preferred for showing and intense inhibitory effect towards the subunit α2δ-1 of voltage-gated calcium channels (VGCC):

[1] 3-(3-((Benzyl(ethyl)amino)methyl)phenoxy)-N-methyl-3-(thiophen-2-yl)propan-1-amine,

[2] 3-(3-((Benzylamino)methyl)phenoxy)-N-methyl-3-(thiophen-2-yl)propan-1-amine,

[3] N-methyl-3-(3-((methylamino)methyl)phenoxy)-3-(thiophen-2-yl)propan-1-amine,

[4] 3-(3-((Dimethylamino)methyl)phenoxy)-N-methyl-3-(thiophen-2-yl)propan-1-amine,

[5] 3-(3-((Ethylamino)methyl)phenoxy)-N-methyl-3-(thiophen-2-yl)propan-1-amine,

[6] 3-(3-((Benzyl(methyl)amino)methyl)phenoxy)-N-methyl-3-(thiophen-2-yl)propan-1-amine,

[7] 3-(3-(Methylamino)-1-(thiophen-2-yl)propoxy)-N-(pyridin-2-ylmethyl)benzamide,

[8] 3-(3-(Methylamino)-1-(thiophen-2-yl)propoxy)-N-(pyridin-3-yl)benzamide,

[9] N-(3-(5-methyl-1,3,4-oxadiazol-2-yl)phenyl)-3-(3-(methylamino)-1-(thiophen-2-yl)propoxy)benzamide,

[10] N-benzyl-3-(3-(methylamino)-1-(thiophen-2-yl)propoxy)benzamide,

[11] N-(2-((dimethylamino)methyl)phenyl)-3-(3-(methylamino)-1-(thiophen-2-yl)propoxy)benzamide,

[12] N-(2-(dimethylamino)phenyl)-3-(3-(methylamino)-1-(thiophen-2-yl)propoxy)benzamide,

[13] 3-(3-(Methylamino)-1-phenylpropoxy)-N-phenylbenzamide,

[14] N-(3-(5-methyl-1,3,4-oxadiazol-2-yl)phenyl)-3-(3-(methylamino)-1-phenylpropoxy)benzamide,

[15] 3-(3-(Methylamino)-1-phenylpropoxy)-N-(pyridin-3-yl)benzamide,

[16] N-methyl-3-(3-(methylamino)-1-phenylpropoxy)benzamide,

[17] N-benzyl-3-(3-(methylamino)-1-phenylpropoxy)benzamide,

[18] 3-(3-(Methylamino)-1-phenylpropoxy)-N-(pyridin-2-ylmethyl)benzamide,
[19] N-ethyl-3-(3-(methylamino)-1-phenylpropoxy)benzamide,
[20] 3-(3-(Methylamino)-1-phenylpropoxy)-N-(2-(methylamino)ethyl)benzamide,
[21] N-(6-(ethylamino)pyridin-3-yl)-3-(3-(methylamino)-1-phenylpropoxy)benzamide,
[22] 3-(3-(Methylamino)-1-phenylpropoxy)-N-(1-methylpiperidin-4-yl)benzamide,
[23] N-methyl-N-(3-(3-(methylamino)-1-phenylpropoxy)phenyl)benzamide,
[24] N-methyl-N-(3-(3-(methylamino)-1-phenylpropoxy)phenyl)acetamide,
[25] N-methyl-N-(3-(3-(methylamino)-1-phenylpropoxy)phenyl)butyramide,
[26] N-methyl-N-(3-(3-(methylamino)-1-phenylpropoxy)phenyl)nicotinamide,
[27] 3-(Aminomethyl)-N-methyl-N-(3-(3-(methylamino)-1-phenylpropoxy)phenyl)benzamide,
[28] 4-Amino-N-methyl-N-(3-(3-(methylamino)-1-phenylpropoxy)phenyl)butanamide,
[29] 2-(Ethylamino)-N-methyl-N-(3-(3-(methylamino)-1-phenylpropoxy)phenyl)-4-(pyrrolidin-1-yl)pyrimidine-5-carboxamide,
[30] 2-(Ethylamino)-N-methyl-N-(3-(3-(methylamino)-1-(thiophen-2-yl)propoxy)phenyl)-4-(pyrrolidin-1-yl)pyrimidine-5-carboxamide,
[31] N-methyl-N-(3-((3-(methylamino)-1-phenylpropoxy)methyl)phenyl)benzamide,
[32] N-methyl-N-(3-((3-(methylamino)-1-phenylpropoxy)methyl)phenyl)nicotinamide,
[33] 2-Methoxy-N-methyl-N-(3-((3-(methylamino)-1-phenylpropoxy)methyl)phenyl)pyrimidine-5-carboxamide,
[34] N-methyl-N-(3-((3-(methylamino)-1-phenylpropoxy)methyl)phenyl)pyrimidine-5-carboxamide,
[35] N-methyl-N-(3-((3-(methylamino)-1-phenylpropoxy)methyl)phenyl)-2-(methylthio)pyrimidine-5-carboxamide,
[36] N-methyl-N-(3-((3-(methylamino)-1-phenylpropoxy)methyl)phenyl)picolinamide,
[37] 2-(Ethylamino)-N-methyl-N-(3-((3-(methylamino)-1-phenylpropoxy)methyl)phenyl)-4-(pyrrolidin-1-yl)pyrimidine-5-carboxamide,
[38] 2-(Ethylamino)-N-methyl-N-(3-((3-(methylamino)-1-(thiophen-2-yl)propoxy)methyl)phenyl)-4-(pyrrolidin-1-yl)pyrimidine-5-carboxamide,
[39] N-(3-((3-(methylamino)-1-phenylpropoxy)methyl)phenyl)benzamide,
[40] N-(3-((3-(methylamino)-1-phenylpropoxy)methyl)phenyl)nicotinamide,
[41] 2-Methoxy-N-(3-((3-(methylamino)-1-phenylpropoxy)methyl)phenyl)pyrimidine-5-carboxamide,
[42] N-(3-((3-(methylamino)-1-phenylpropoxy)methyl)phenyl)pyrimidine-5-carboxamide,
[43] N-(3-((3-(methylamino)-1-phenylpropoxy)methyl)phenyl)picolinamide,
[44] N-(3-((3-(methylamino)-1-phenylpropoxy)methyl)phenyl)-2-(methylthio)pyrimidine-5-carboxamide,
[45] 2-(Ethylamino)-N-(3-((3-(methylamino)-1-phenylpropoxy)methyl)phenyl)-4-(pyrrolidin-1-yl)pyrimidine-5-carboxamide,
[46] N-(3-((3-(methylamino)-1-(thiophen-2-yl)propoxy)methyl)phenyl)benzamide,
[47] 2-(Dimethylamino)-N-(3-((3-(methylamino)-1-(thiophen-2-yl)propoxy)methyl)phenyl)benzamide,
[48] 2-Fluoro-N-(3-((3-(methylamino)-1-(thiophen-2-yl)propoxy)methyl)phenyl)benzamide,
[49] 2-(Ethylamino)-N-(3-((3-(methylamino)-1-(thiophen-2-yl)propoxy)methyl)phenyl)-4-(pyrrolidin-1-yl)pyrimidine-5-carboxamide,
[50] 2-(Ethylamino)-N-(3-(3-(methylamino)-1-phenylpropoxy)phenyl)-4-(pyrrolidin-1-yl)pyrimidine-5-carboxamide,
[51] 2-(Ethylamino)-N-(3-(3-(methylamino)-1-(thiophen-2-yl)propoxy)phenyl)-4-(pyrrolidin-1-yl)pyrimidine-5-carboxamide,
[52] N-benzyl-3-((3-(methylamino)-1-phenylpropoxy)methyl)aniline,
[53] 3-((3-(Methylamino)-1-phenylpropoxy)methyl)-N-(pyrimidin-5-ylmethyl)aniline,
[54] N-(3-((3-(dimethylamino)-1-(thiophen-2-yl)propoxy)methyl)phenyl) benzamide,
[55] 2-(Dimethylamino)-N-(3-((3-(dimethylamino)-1-(thiophen-2-yl)propoxy)methyl)phenyl)benzamide,
[56] N-ethyl-N-(3-(3-(methylamino)-1-(thiophen-2-yl)propoxy)benzyl) benzamide,
[57] N-Benzyl-N-(3-((3-(methylamino)-1-phenylpropoxy)methyl)phenyl) acetamide,
[58] 3-((3-(Methylamino)-1-phenylpropoxy)methyl)-N-phenylaniline,
[59] N-(3-((3-(methylamino)-1-phenylpropoxy)methyl)phenyl)pyrimidin-2-amine,
[60] 2-(Ethylamino)-N-methyl-N-(3-(3-(methylamino)-1-phenylpropoxy) phenyl)pyrimidine-5-carboxamide,
[61] N-(3-((3-(methylamino)-1-phenylpropoxy)methyl)phenyl)-N-phenylacetamide,
[62] N-methyl-N-(3-(3-(methylamino)-1-(thiophen-2-yl)propoxy) phenyl)acetamide,
[63] N-methyl-N-(3-(3-(methylamino)-1-(thiophen-2-yl)propoxy)phenyl)benzamide,
[64] N-methyl-N-(3-(3-(methylamino)-1-(thiophen-2-yl)propoxy)phenyl)butyramide,
[65] N-methyl-N-(3-(3-(methylamino)-1-(thiophen-2-yl)propoxy)phenyl)nicotinamide,
[66] N-(3-(3-(methylamino)-1-(thiophen-2-yl)propoxy)phenyl)benzamide,
[67] N-methyl-N-(3-(3-(methylamino)-1-(thiophen-2-yl)propoxy)phenyl)benzamide,
[68] N-methyl-N-(3-(3-(methylamino)-1-phenylpropoxy)phenyl)nicotinamide and
[69] N-methyl-N-(3-(3-(methylamino)-1-phenylpropoxy)phenyl)benzamide;

or a pharmaceutically acceptable salt, isomer, prodrug or solvate thereof.

Among compounds of general formula (I) some subgroups of compounds have shown in addition a dual affinity towards the subunit α2δ-1 of voltage-gated calcium channels (VGCC) and the noradrenaline transporter (NET). These compounds having dual affinity represent the preferred embodiments of the invention and are represented among one of the following of formula (Ic), (Id), (Ie), (If) or (Ig):

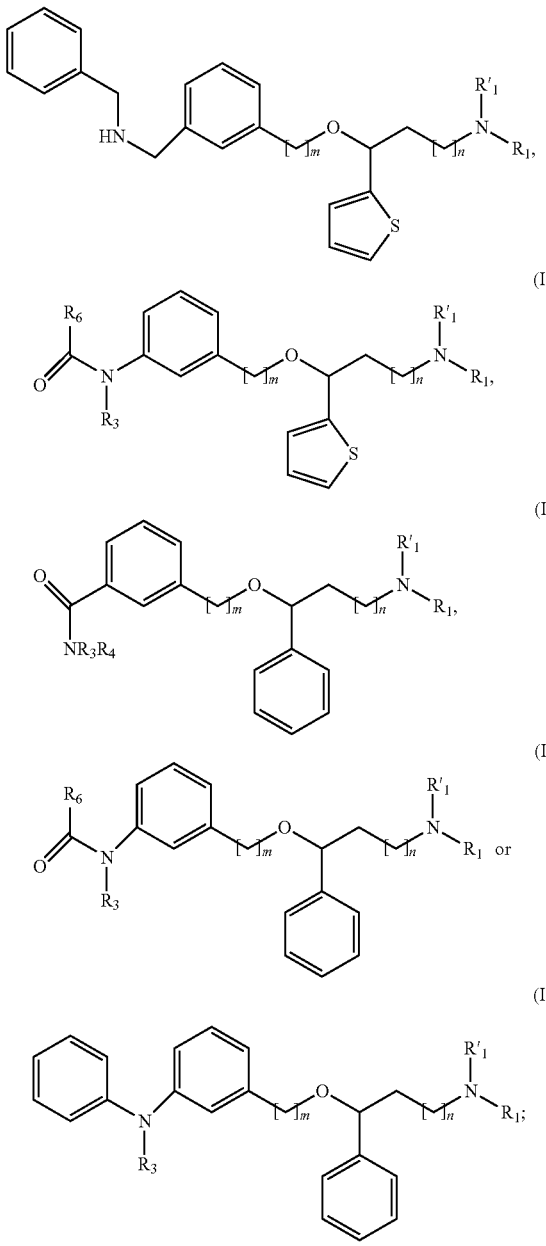

wherein $R_1$, $R'_1$, $R_3$, $R_4$, $R_6$, m and n are as defined in claim 1.

The preferred compounds of the invention showing dual inhibitory effect towards the subunit α2δ-1 of voltage-gated calcium channels (VGCC) and the noradrenaline transporter (NET) are selected from the following group:

[2]  3-(3-((Benzylamino)methyl)phenoxy)-N-methyl-3-(thiophen-2-yl)propan-1-amine,
[6]  3-(3-((Benzyl(methyl)amino)methyl)phenoxy)-N-methyl-3-(thiophen-2-yl)propan-1-amine,
[13] 3-(3-(Methylamino)-1-phenylpropoxy)-N-phenylbenzamide,
[14] N-(3-(5-methyl-1,3,4-oxadiazol-2-yl)phenyl)-3-(3-(methylamino)-1-phenylpropoxy)benzamide,
[15] 3-(3-(Methylamino)-1-phenylpropoxy)-N-(pyridin-3-yl)benzamide,
[17] N-benzyl-3-(3-(methylamino)-1-phenylpropoxy)benzamide,
[18] 3-(3-(Methylamino)-1-phenylpropoxy)-N-(pyridin-2-ylmethyl)benzamide,
[20] 3-(3-(Methylamino)-1-phenylpropoxy)-N-(2-(methylamino)ethyl)benzamide,
[22] 3-(3-(Methylamino)-1-phenylpropoxy)-N-(1-methylpiperidin-4-yl)benzamide,
[27] 3-(Aminomethyl)-N-methyl-N-(3-(3-(methylamino)-1-phenylpropoxy)phenyl)benzamide,
[28] 4-Amino-N-methyl-N-(3-(3-(methylamino)-1-phenylpropoxy)phenyl)butanamide,
[38] 2-(Ethylamino)-N-methyl-N-(3-((3-(methylamino)-1-(thiophen-2-yl)propoxy)methyl)phenyl)-4-(pyrrolidin-1-yl)pyrimidine-5-carboxamide,
[39] N-(3-((3-(methylamino)-1-phenylpropoxy)methyl)phenyl)benzamide,
[41] 2-Methoxy-N-(3-((3-(methylamino)-1-phenylpropoxy)methyl)phenyl)pyrimidine-5-carboxamide,
[43] N-(3-((3-(methylamino)-1-phenylpropoxy)methyl)phenyl)picolinamide,
[46] N-(3-((3-(methylamino)-1-(thiophen-2-yl)propoxy)methyl)phenyl)benzamide,
[48] 2-Fluoro-N-(3-((3-(methylamino)-1-(thiophen-2-yl)propoxy)methyl)phenyl)benzamide,
[50] 2-(Ethylamino)-N-(3-(3-(methylamino)-1-phenylpropoxy)phenyl)-4-(pyrrolidin-1-yl)pyrimidine-5-carboxamide and
[58] 3-((3-(Methylamino)-1-phenylpropoxy)methyl)-N-phenylaniline;

or a pharmaceutically acceptable salt, isomer, prodrug or solvate thereof.

In another preferred embodiment, the compounds showing a dual affinity towards the subunit α2δ-1 of voltage-gated calcium channels (VGCC) and the noradrenaline transporter (NET) are selected from:

[70] 3-(4-((Benzyl(methyl)amino)methyl)-3-fluorophenoxy)-N-methyl-3-(thiophen-2-yl)propan-1-amine and
[71] 3-(4-((Benzylamino)methyl)-3-fluorophenoxy)-N-methyl-3-(thiophen-2-yl)propan-1-amine;

or a pharmaceutically acceptable salt, isomer, prodrug or solvate thereof.

In another aspect, the invention refers to the processes for obtaining the compounds of general formula (I). Several procedures have been developed for obtaining all the compounds of the invention, and the procedures will be explained below in methods A, B and C.

The obtained reaction products may, if desired, be purified by conventional methods, such as crystallization and chromatography. Where the processes described below for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

Method A

Method A represents a first process for synthesizing compounds according to general formula (I). Method A allows for the preparation of compounds of general formula (Ia) that is compounds of formula (I) where m is 0. There are described two methods for obtaining compounds of formula (Ia), namely method A1 and A2.

Method A1

In this sense, a process is described for the preparation of a compound of general formula (Ia):

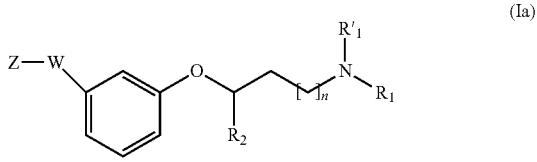

(Ia)

comprising:
the reaction of a compound of formula (IIa):

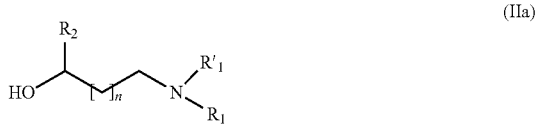

(IIa)

with a either compound of formula (IIIa) or (IIIb):

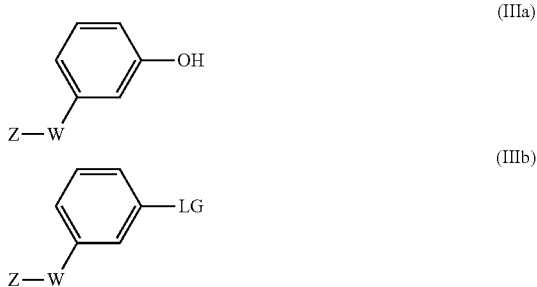

(IIIa)

(IIIb)

wherein $R_1$, $R'_1$, $R_2$, W, Z and n are as defined before and LG is a suitable leaving group such as chloro, bromo, iodo, mesylate, tosylate, nosylate or triflate.

In the case where the reaction is carried out between a compound of formula (IIa) with an hydroxyl compound of formula (IIIa), the reaction is performed under conventional Mitsunobu conditions by treating an alcohol of formula (IIa) with a compound of formula (IIIa) in the presence of an azo compound such as, 1,1'-(azodicarbonyl)dipiperidine (ADDP), diisopropylazodicarboxylate (DIAD) or diethyl azodicarboxylate (DEAD) and a phosphine such as tributylphosphine or triphenylphoshine. The Mitsunobu reaction is carried out in a suitable solvent, such as toluene or tetrahydrofuran (THF); at a suitable temperature comprised between 0° C. and the reflux temperature, preferably at room temperature, or alternatively, the reactions can be carried out in a microwave reactor.

Whenever the reaction is carried out between a compound of formula (IIa) and a compound of formula (IIIb), the reaction is performed under conventional aromatic nucleophilic substitution conditions by treating an alcohol of formula (IIa) with a compound of formula (IIIb) wherein LG represents a leaving group (preferably fluoro), in the presence of a strong base such as sodium hydride. The reaction is preferably carried out in a suitable solvent, such as a polar aprotic solvent, preferably dimethylformamide (DMF) or dimethylacetamide; at a suitable temperature comprised between room temperature and the reflux temperature, preferably heating, or alternatively, the reactions can be carried out in a microwave reactor. Alternatively, when LG is triflate, bromo or iodo, the compound of formula (IIIb) can be introduced under cross-coupling conditions, using a Pd or Cu catalyst and a suitable ligand.

Compound of formula (IIa) is commercially available or can be obtained by reduction of the corresponding ketones, preferably using a hydride source. In addition, the reduction can be performed under asymmetric conditions described in the literature to render chiral compounds of formula IIa in enantiopure form. As a way of example, the chiral reduction can be performed using a hydride source such as borane-tetrahydrofuran complex or borane-dimethyl sulfide complex, in the presence of a Corey-Bakshi-Shibata oxazaborolidine catalyst, in a suitable solvent such as tetrahydrofuran or toluene, at a suitable temperature, preferably comprised between 0° C. and room temperature.

Alternatively compound of formula (IIa) can be obtained by deprotection of a compound of formula (IIa)-P (see scheme 1) protected with with any suitable protecting group (P), such as for example Boc (tert-butoxycarbonyl) or Teoc (2-(trimethylsilyl)ethoxycarbonyl). Boc or Teoc deprotection can be effected by any suitable method, such as treatment with an acid, preferably HCl or trifluoroacetic acid in an appropriate solvent such as 1,4-dioxane, dichloromethane (DCM), ethyl acetate or a mixture of an organic solvent and water; alternatively by treatment with $ZnBr_2$ in an organic solvent, preferably DCM. Alternatively, for Teoc deprotection, by reaction with CsF in an organic solvent, preferably DMF at a temperature range of 20-130° C., alternatively under microwaves irradiation.

Also compound (IIa) can be obtained by incorporation of the amino group into a compound of formula (IIa)-LG by an alkylation reaction with compound (VI) (see scheme 1). The alkylation reaction is carried out in a suitable solvent, such as ethanol, dimethylformamide, dimethylsulfoxide (DMSO), acetonitrile (ACN) or a mixture of an organic solvent and water, preferably ethanol; optionally in the presence of a base such as $K_2CO_3$ or triethylamine (TEA); at a suitable temperature comprised between room temperature and the reflux temperature, preferably heating, or alternatively, the reactions can be carried out in a microwave reactor. Additionally, an activating agent such as sodium iodide or potassium iodide can be used.

Compounds of formula (IIIa), (IIIb) or (VI) are commercially available or can be prepared by conventional methods described in the bibliography.

Method A2

A further alternative process for the preparation of a compound of general formula (Ia) comprises the reaction of a compound of formula (IV-LG):

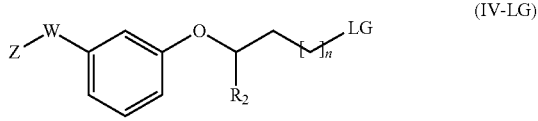

(IV-LG)

with a compound of formula (VI):

(VI)

wherein $R_1$, $R'_1$, $R_2$, W, Z and n are as defined before and LG represents a suitable leaving group such as chloro, bromo, iodo, mesylate, tosylate, nosylate or triflate.

The alkylation reaction is carried out in a suitable solvent, such as ethanol, dimethylformamide, dimethylsulfoxide, acetonitrile or a mixture of an organic solvent and water, preferably ethanol; optionally in the presence of a base such as $K_2CO_3$ or triethylamine; at a suitable temperature comprised between room temperature and the reflux temperature, preferably heating, or alternatively, the reactions can be carried out in a microwave reactor. Additionally, an activating agent such as sodium iodide or potassium iodide can be used.

Compound of formula (IV)-LG can be prepared by reaction of a compound of formula (IIb) where LG represents a leaving group (such as chloro, bromo, iodo, mesylate, tosylate, nosylate or triflate with a compound of formula (IIIa) (see scheme 1). The reaction is carried out preferably in the presence of a base, such as sodium hydride. The alkylation reaction is carried out in a suitable solvent, such as tetrahydrofuran or dimethylformamide, at a suitable temperature comprised between 0° C. and the reflux temperature, preferably at room temperature.

Method B

Method B represents a process for synthesizing compounds according to general formula (Ib), namely compounds of general formula (I) where m is 1. There are described two methods for obtaining compounds of formula (Ib), namely method B1 and B2.

Method B1

In this sense, a first process is described preparation of a compound of general formula (Ib):

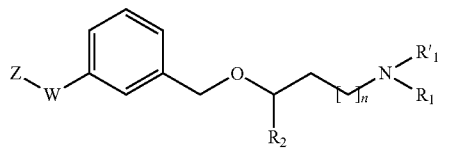
(Ib)

comprising the reaction between a compound of formula (IIa):

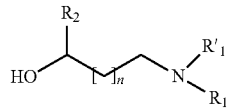
(IIa)

with a compound of formula (IIIc):

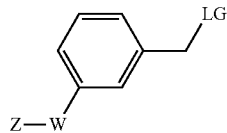
(IIIc)

wherein $R_1$, $R'_1$, $R_2$, W, Z and n are as defined before and LG represents a suitable leaving group such as chloro, bromo, iodo, mesylate, tosylate, nosylate or triflate.

The reaction between the compound of formula (IIa) with an alkylating agent of formula (IIIc) is carried out in the presence of a strong base such as sodium hydride or potassium tert-butoxide. The alkylation reaction is preferably carried out in a suitable solvent, such as tetrahydrofuran or dimethylformamide, at a suitable temperature comprised between 0° C. and the reflux temperature, preferably room temperature, or alternatively, the reactions can be carried out in a microwave reactor. Additionally, an activating agent such as sodium iodide or a phase transfer catalyst such as tetrabutylammonium iodide can be used.

Method B2

The second method for preparing compounds of formula (Ib) comprises the deprotection of a compound of formula (V-P):

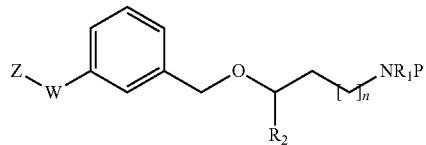
(V-P)

wherein $R_1$, $R'_1$, $R_2$, W, Z and n are as defined before and P represents a protecting group such as, for example, Boc (tert-butoxycarbonyl) or Teoc (2-(trimethylsilyl)ethoxycarbonyl).

Boc or Teoc deprotection can be effected by any suitable method, such as treatment with an acid, preferably HCl or trifluoroacetic acid in an appropriate solvent such as 1,4-dioxane, DCM, ethyl acetate or a mixture of an organic solvent and water; alternatively by treatment with $ZnBr_2$ in an organic solvent, preferably DCM. Alternatively, for Teoc deprotection, by reaction with CsF in an organic solvent, preferably DMF at a temperature range of 20-130° C., alternatively under microwaves irradiation.

Scheme 1 below summarizes the synthetic routes of methods A (including A1 and A2) and B (including B1 and B2).

Scheme 1

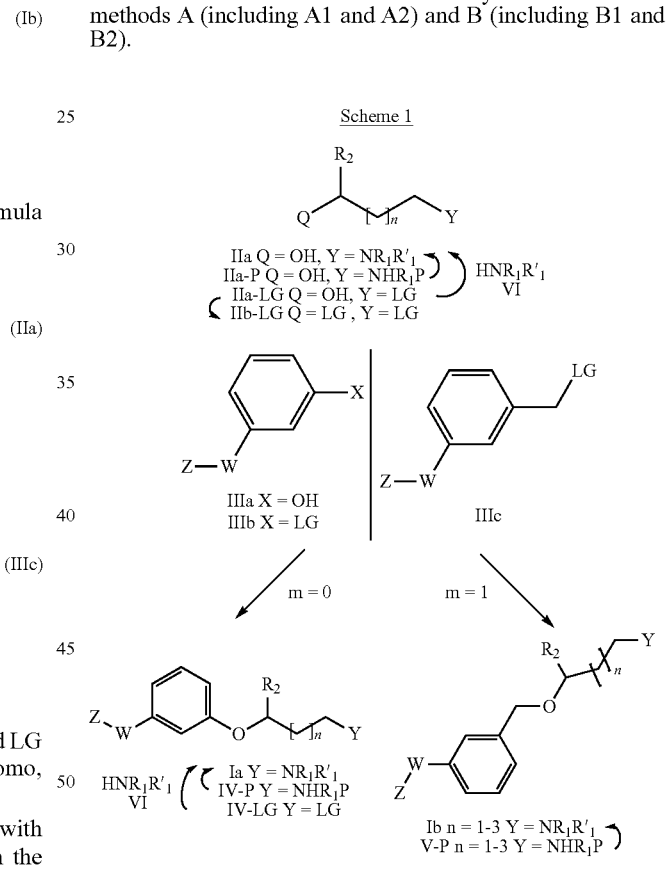

Method C

Method C represents the third process for synthesizing compounds according to general formula (I).

In this sense, there is provided a process for the preparation of a compound of general formula (I):

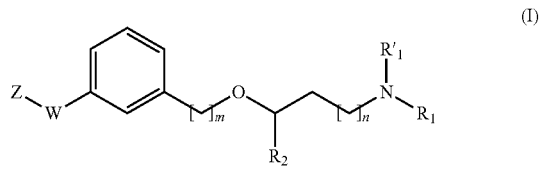
(I)

starting from a compound of formula (VII):

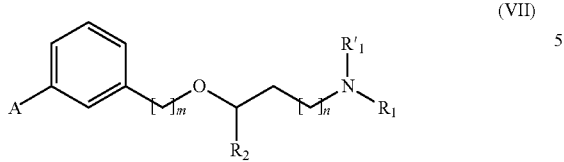

(VII)

wherein $R_1$, $R'_1$, $R_2$, W, Z, m and n are as defined before and where A may represent an aldehyde, a carboxylic acid, a nitro group or a suitable leaving group or —$(CH_2)_p$-LG wherein LG represents a suitable leaving group and p is 1 or 2 and where the reaction is dependent on the nature of A and W resulting in that the reaction comprises:

- a reductive amination reaction in the presence of a reductive agent when A is an aldehyde and W is —$(CH_2)_p$—;
- the reaction in the presence of a carboxilic acid activating reagent when A is a carboxilic acid and W is a —C(O)— group;
- a coupling reaction in the presence of a metal catalyst when A is a good leaving group and W is a bond;
- a reduction reaction when A is a nitro group and W is a bond; or
- a reaction in the presence of a base when A is —$(CH_2)_p$-LG group and W is a —$(CH_2)_p$— group.

As explained above, the reaction of an intermediate of general formula (VII) or its counterparts VII-P and VII-LG (see scheme 2 below) to give a compound of formula I (or its counterparts IV/V-P and IV/V-LG, respectively) may be carried out under different reaction conditions, depending on the nature of the groups A and Z—W:

When A is an aldehyde and W is —$(CH_2)_p$—, by reductive amination reaction in the presence of a reductive reagent, preferably sodium triacetoxyborohydride, in the presence of a base, preferably diisopropylethylamine (DIPEA) or triethylamine (TEA), in an organic solvent, preferably 1,2-dichloroethane (DCE).

When A is a carboxylic acid and W is —C(O)—, in the presence of a carboxylic acid activating reagent, preferably HATU (2-(7-Aza-1H-benzotriazole-1-yl)-1,1,3,3-tetramethyluronium) or EDCl (N-(3-Dimethylaminopropyl)-N'-ethylcarbodiimide hydrochloride), in the presence of a base, preferably DIPEA (N,N-Diisopropylethylamine) or TEA, in an organic solvent, preferably dichloromethane (DCM). Alternatively, by conversion to the acid chloride intermediate using any suitable method.

When A is a good leaving group as a halogen atom and W is a bond, using a metal catalysed coupling, for example, in the presence of a copper salt as catalyst, preferably CuI, an appropriate ligand, preferably N1,N2-dimethylethane-1,2-diamine or proline, and an inorganic base, preferably $K_3PO_4$ or $K_2CO_3$ in an organic solvent, preferably 1,4-dioxane, N,N-dimethylformamide (DMF) or DMSO, at a temperature range of 80-130° C. Alternatively, in the presence of copper powder, in a polar solvent, preferably water, at a temperature range 80° C. and the reflux temperature. Alternatively, in the presence of a Pd catalyst, preferably $Pd_2(dba)_3$ and a suitable ligand, preferably 2-dicyclohexylphosphino-2',4',6'-triisopropylbiphenyl (Xphos), in the presence of a base, preferably NaOtBu, in an organic solvent, preferably toluene or 1,4-dioxane, at a temperature range of 50-150° C.

When A is a nitro group and W is a bond, by reduction reaction using any suitable method, preferably using iron powder, in a polar solvent, preferably EtOH, in the presence of $NH_4Cl$ as additive, at a suitable temperature, preferably comprised between room temperature and the reflux temperature; followed by additional derivatization reactions, as for example by reductive amination, or by reaction with a carboxylic acid, acid chloride or carboxylic anhydride under standard experimental conditions.

When A is a —$(CH_2)_p$-LG group (where LG is a good leaving group as a halogen atom or sulfonate), and W is $(CH_2)_p$, the reaction may be carried out in the presence of a base, preferably NaH, DIPEA or TEA, in an organic solvent, preferably DMF or THF, at a suitable temperature, preferably in the range of 0-100° C. Alternatively, in the presence of tetrabutylammonium iodide (TBAI).

The different synthetic route including method C as well as reactions for preparing the intermediate compounds for such reactions are depicted in scheme 2:

Scheme 2

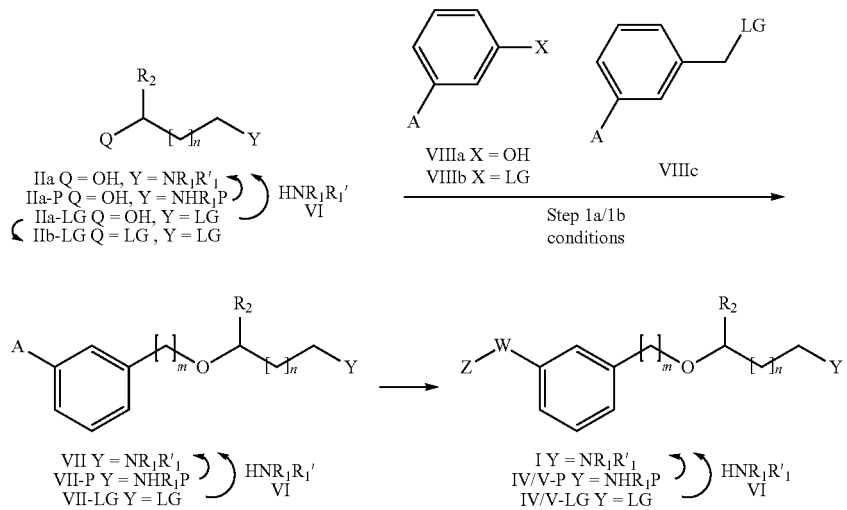

In scheme 2, $R_1$, $R'_1$, $R_2$, W, Z, m and n are as defined before for compounds of formula (I), LG represents a leaving group (such as chloro, bromo, iodo, mesylate, tosylate, nosylate or triflate), P represents a protecting group of the amino function such as Boc (tert-butoxycarbonyl) or Teoc (2-(trimethylsilyl)ethoxycarbonyl) and A represents a suitable function to be converted to a group Z—W—.

Intermediates of type (VII) can be obtained from compounds of formula (IIa) or (II-b) and reagents of formula (VIIIa), (VIII-b) or (VIII-c) using the same reaction conditions as described above in methods A and B.

In turn, intermediates of formula (IIa), (IIa)-P and (IIa)-LG are commercially available or can be obtained by reduction of the corresponding ketones, preferably using a hydride source. In addition, the reduction can be performed under asymmetric conditions described in the literature to render chiral compounds of formula IIa in enantiopure form. As a way of example, the chiral reduction can be performed using a hydride source such as borane-tetrahydrofuran complex or borane-dimethyl sulfide complex, in the presence of a Corey-Bakshi-Shibata oxazaborolidine catalyst, in a suitable solvent such as tetrahydrofuran or toluene, at a suitable temperature, preferably comprised between 0° C. and room temperature.

The compounds of general formula (IIb)-LG are commercially available or can be obtained from compounds of formula (IIa)-LG by conventional methods described in the bibliography. For example, using methanesulfonyl chloride in an organic solvent, preferably DCM, in the presence of a base, preferably TEA or DIPEA, at a temperature range of 0° C. and room temperature.

The compounds of general formula (VI), (VIII-a), (VIII-b) and (VIII-a) are commercially available or can be prepared by conventional methods described in the bibliography. Moreover, certain compounds of the present invention can also be obtained starting from other compounds of formula (I) by appropriate conversion reactions of functional groups, in one or several steps, using well-known reactions in organic chemistry under standard experimental conditions.

In addition, a compound of formula (I) that shows chirality can also be obtained by resolution of a racemic compound of formula (I) either by chiral preparative HPLC or by crystallization of a diastereomeric salt or co-crystal. Alternatively, the resolution step can be carried out at a previous stage, using any suitable intermediate.

Another aspect of the invention refers to the process for obtaining the compounds [70] and [71] using the method A described above.

Turning to another aspect, the invention also relates to the therapeutic use of the compounds of general formula (I). As mentioned above, compounds of general formula (I) show a strong affinity to the subunit $\alpha 2\delta$ and more preferably to the $\alpha 2\delta$-1 subunit of voltage-gated calcium channels. In a more preferred embodiment of the invention compounds of general formula (I) show a strong affinity to both the subunit $\alpha 2\delta$ and more preferably to the $\alpha 2\delta$-1 subunit of voltage-gated calcium channels as well as to the noradrenaline transporter (NET) and can behave as agonists, antagonists, inverse agonists, partial antagonists or partial agonists thereof. Therefore, compounds of general formula (I) are useful as medicaments.

They are suitable for the treatment and/or prophylaxis of diseases and/or disorders mediated by the subunit $\alpha 2\delta$, especially the $\alpha 2\delta$-1 subunit of voltage-gated calcium channels and/or the noradrenaline transporter (NET). In this sense, compounds of formula (I) are suitable for the treatment and/or prophylaxis of pain, especially neuropathic pain, inflammatory pain, and chronic pain or other pain conditions involving allodynia and/or hyperalgesia, depression, anxiety and attention-deficit-/hyperactivity disorder (ADHD).

The compounds of formula (I) are especially suited for the treatment of pain, from medium to severe pain, visceral pain, chronic pain, cancer pain, migraine, inflammatory pain, acute pain or neuropathic pain, allodynia or hyperalgesia. This may include mechanical allodynia or thermal hyperalgesia.

PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

In a preferred embodiment compounds of the invention are used for the treatment and/or prophylaxis of allodynia and more specifically mechanical or thermal allodynia.

In another preferred embodiment compounds of the invention are used for the treatment and/or prophylaxis of hyperalgesia.

In yet another preferred embodiment compounds of the invention are used for the treatment and/or prophylaxis of neuropathic pain and more specifically for the treatment and/or prophylaxis of hyperpathia.

A related aspect of the invention refers to the use of compounds of formula (I) for the manufacture of a medicament for the treatment and/or prophylaxis of disorders and diseases mediated by the subunit $\alpha 2\delta$, especially the $\alpha 2\delta$-1 subunit of voltage-gated calcium channels and/or the noradrenaline transporter (NET), as explained before.

Another related aspect of the invention refers to a method for the treatment and/or prophylaxis of disorders and diseases mediated by the subunit $\alpha 2\delta$, especially the $\alpha 2\delta$-1 subunit of voltage-gated calcium channels and/or the noradrenaline transporter (NET), as explained before comprising the administration of a therapeutically effective amount of a compound of general formula (I) to a subject in need thereof.

Another aspect of the invention is a pharmaceutical composition, which comprises at least a compound of general formula (I) or a pharmaceutically acceptable salt, prodrug, isomer or solvate thereof, and at least a pharmaceutically acceptable carrier, additive, adjuvant or vehicle.

The pharmaceutical composition of the invention can be formulated as a medicament in different pharmaceutical forms comprising at least a compound binding to the subunit $\alpha 2\delta$, especially the $\alpha 2\delta$-1 subunit of voltage-gated calcium channels and/or the noradrenaline transporter (NET) and optionally at least one further active substance and/or optionally at least one auxiliary substance.

The auxiliary substances or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously.

Preferably, the composition is suitable for oral or parenteral administration, more preferably for oral, intravenous, intraperitoneal, intramuscular, subcutaneous, intrathekal, rectal, transdermal, transmucosal or nasal administration.

The composition of the invention can be formulated for oral administration in any form preferably selected from the group consisting of tablets, dragées, capsules, pills, chewing gums, powders, drops, gels, juices, syrups, solutions and suspensions. The composition of the present invention for oral administration may also be in the form of multiparticulates, preferably microparticles, microtablets, pellets or granules, optionally compressed into a tablet, filled into a capsule or suspended in a suitable liquid. Suitable liquids are known to those skilled in the art.

Skin applications include ointments, gels, creams, lotions, suspensions or emulsions.

The preferred form of rectal application is by means of suppositories.

In a preferred embodiment, the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the apropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

The following examples are merely illustrative of certain embodiments of the invention and cannot be considered as restricting it in any way.

EXAMPLES

In the next preparation examples the preparation of both intermediates compounds as well as compounds according to the invention are disclosed.

The following abbreviations are used in the examples:
ACN: Acetonitrile
Anh: Anhydrous
Aq: Aqueous
Conc: Concentrated
CH: Cyclohexane
DCM: Dichloromethane
DCE: 1,2-Dichloroethane
DEA: Diethylamine
DIAD: Diisopropyl azodicarboxylate
DIBAL: Diisobutylaluminium hydride
DIPEA: N,N-Diisopropylethylamine
DMA: N,N-Dimethylacetamide
DMSO: Dimethylsulfoxide
EtOAc: Ethyl acetate
EtOH: Ethanol
Ex: Example
h: Hour/s
HATU: 2-(7-Aza-1H-benzotriazole-1-yl)-1,1,3,3-tetramethyluronium
Hex: Hexane
HPLC: High-performance liquid chromatography
INT: Intermediate
IPA: Isopropanol
MeOH: Methanol
MS: Mass spectrometry
Min: Minutes
PPh$_3$: Triphenylphosphine
Quant: Quantitative
Ret: Retention
rt: Room temperature
Sat: Saturated
TBAF: Tetrabutylammonium fluoride
TBAI: Tetrabutylammonium iodide
TEA: Et$_3$N, Triethylamine
TFA: Trifluoroacetic acid
THF: Tetrahydrofuran
XPhos: 2-Dicyclohexylphosphino-2',4',6'-triisopropylbiphenyl
Wt: Weight The following methods were used to generate the HPLC or HPLC-MS data:

Method A: Column Eclipse XDB-C18 4.6×150 mm, 5 μm; flow rate 1 mL/min; A: H$_2$O (0.05% TFA); B: ACN; Gradient: 5% to 95% B in 7 min, isocratic 95% B 5 min.

Method B: Column Zorbax SB-C18 2.1×50 mm, 1.8 μm; flow rate 0.5 mL/min; A: H$_2$O (0.1% formic acid); B: ACN (0.1% formic acid); Gradient: 5% to 95% B in 4 min, isocratic 95% B 4 min.

PREPARATION EXAMPLES

Example 1: 3-(3-((Benzyl(ethyl)amino)methyl)phenoxy)-N-methyl-3-(thiophen-2-yl)propan-1-amine

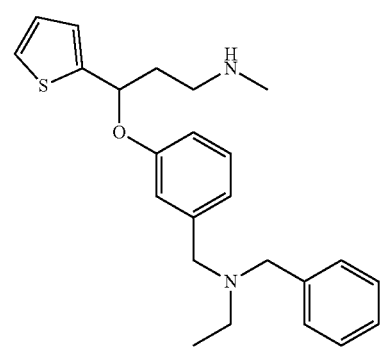 [SMILES: CCN(Cc1ccccc1)Cc1cccc(OC(CCNC)c2cccs2)c1]

a) 3-(3-Chloro-1-(thiophen-2-yl)propoxy)benzaldehyde

To a solution of 3-chloro-1-(thiophen-2-yl)propan-1-ol (1.00 g, 5.66 mmol) in THF (10 mL) 3-hydroxybenzaldehyde (0.69 g, 5.66 mmol) and PPh$_3$ (1.63 g, 6.23 mmol) were added. The mixture was cooled to 0° C. and then DIAD (1.26 g, 6.23 mmol) was added dropwise. The reaction mixture was warmed slowly at rt and stirred for 16 h. The solvent was removed under vacuum and the residue was purified by flash chromatography, silica gel, gradient CH to 100% EtOAc to afford the title compound (700 mg, 44% yield). HPLC (Method B): Ret, 5.56 min; ESI$^+$-MS m/z, 281.2 (M+H).

b) N-benzyl-N-(3-(3-chloro-1-(thiophen-2-yl)propoxy)benzyl)ethanamine

To a solution of the compound obtained in step a (80 mg, 0.28 mmol) in DCE (2 mL), N-benzylethanamine (58 mg, 0.42 mmol) and NaBH(OAc)$_3$ (121 mg, 0.57 mmol) were added and the mixture was stirred at rt for 16 h. NaHCO$_3$ sat solution was added, the solution was extracted with DCM and the organic layer was concentrated under vacuum to afford the title compound that was used in the next step without further purification (95 mg, 83% yield). HPLC (Method B): Ret, 4.46 min; ESI$^+$-MS m/z, 400.2 (M+H).

c) Title Compound

To a solution of the compound obtained in step b (67 mg, 0.16 mmol) in EtOH (0.2 mL), methylamine (40% water solution, 1.69 mL, 21.7 mmol) was added and the mixture was heated in a sealed tube at 100° C. for 1 h. The mixture was cooled at rt and concentrated under vacuum. Purification by flash chromatography, silica gel, gradient DCM to 40% MeOH afforded the title compound (40 mg, 60% yield). HPLC (Method A): Ret, 4.91 min; ESI$^+$-MS m/z, 395.2 (M+H).

This method was used for the preparation of Ex 2-6 using suitable starting materials:

| EX | Structure | Chemical name | Method | Ret (min) | MS |
|---|---|---|---|---|---|
| 2 | 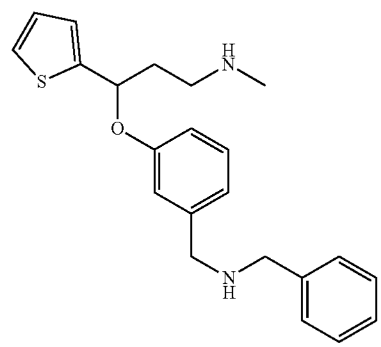 [SMILES: CNCCC(Oc1cccc(CNCc2ccccc2)c1)c1cccs1] | 3-(3-((Benzylamino)methyl)phenoxy)-N-methyl-3-(thiophen-2-yl)propan-1-amine | A | 4.79 | 367.2 (M + H) |
| 3 | 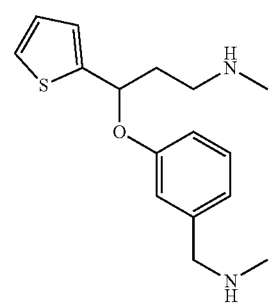 [SMILES: CNCCC(Oc1cccc(CNC)c1)c1cccs1] | N-methyl-3-(3-((methylamino)methyl)phenoxy)-3-(thiophen-2-yl)propan-1-amine | A | 4.10 | 291.1 (M + H) |
| 4 | 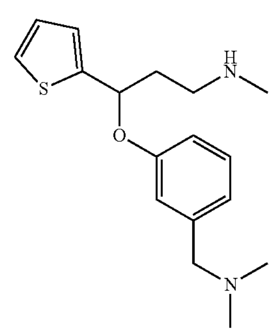 [SMILES: CNCCC(Oc1cccc(CN(C)C)c1)c1cccs1] | 3-(3-((Dimethylamino)methyl)phenoxy)-N-methyl-3-(thiophen-2-yl)propan-1-amine | A | 4.16 | 305.2 (M + H) |

| EX | Structure | Chemical name | Method | Ret (min) | MS |
|---|---|---|---|---|---|
| 5 | 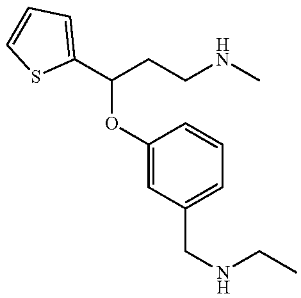 [SMILES: CCNCc1cccc(OC(CCNC)c2cccs2)c1] | 3-(3-((Ethylamino)methyl)phenoxy)-N-methyl-3-(thiophen-2-yl)propan-1-amine | A | 4.16 | 305.2 (M + H) |
| 6 | 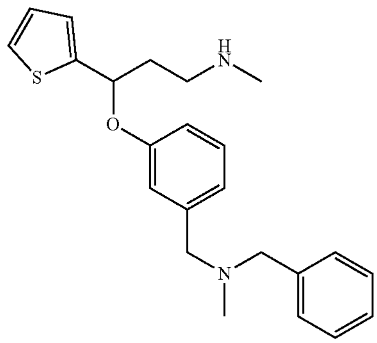 [SMILES: CNCCC(Oc1cccc(CN(C)Cc2ccccc2)c1)c1cccs1] | 3-(3-((Benzyl(methyl)amino)methyl)phenoxy)-N-methyl-3-(thiophen-2-yl)propan-1-amine | A | 4.78 | 381.2 (M + H) |

Example 7: 3-(3-(Methylamino)-1-(thiophen-2-yl)propoxy)-N-(pyridin-2-ylmethyl)benzamide

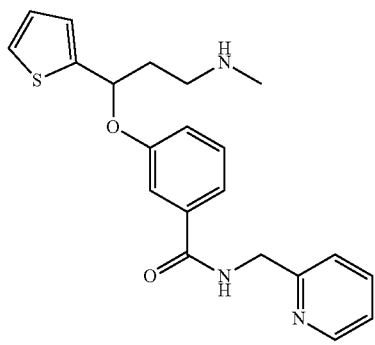 [SMILES: CNCCC(Oc1cccc(C(=O)NCc2ccccn2)c1)c1cccs1]

a) Methyl 3-(3-chloro-1-(thiophen-2-yl)propoxy)benzoate

3-Chloro-1-(thiophen-2-yl)propan-1-ol was treated with methyl 3-hydroxybenzoate in the conditions used in EX 1 step a, to afford the title compound (34% yield). HPLC (Method B): Ret, 5.80 min; ESI⁻-MS m/z, 309.1 (M−H).

b) 3-(3-Chloro-1-(thiophen-2-yl)propoxy)benzoic acid

To a solution of the compound obtained in step a (360 mg, 1.15 mmol) in a (1:1) mixture of THF and water (12 mL), LiOH (166 mg, 6.95 mmol) was added and the mixture was heated at 100° C. for 1 h. The reaction mixture was cooled at rt, citric acid solution was added until pH=5 and extracted with DCM to afford the title compound that was used in the next step without further purification (quant yield). HPLC (Method B): Ret, 5.14 min; ESI⁺-MS m/z, 319.0 (M+Na).

c) 3-(3-Chloro-1-(thiophen-2-yl)propoxy)-N-(pyridin-2-ylmethyl)benzamide

To a solution of the compound obtained in step b (130 mg, 0.43 mmol) in DCM (2 mL), HATU (0.183 g, 0.48 mmol) was added and the mixture was stirred at rt for 30 min. DIPEA (62 mg, 0.48 mmol) and 2-aminomethylpyridine (47 mg, 0.43 mmol) were added and the mixture was stirred at rt for 16 h. DCM was added, washed with water and brine, dried with Na₂SO₄ and the solvent was removed under vacuum. Purification by flash chromatography, silica gel, gradient Hex to 100% EtOAc afforded the title compound (110 mg, 77% yield). HPLC (Method B): Ret, 4.30 min; ESI⁺-MS m/z, 387.1 (M+H).

d) Title Compound

The compound obtained in step c was treated with the conditions used in EX 1 step c to afford the title compound (43% yield). HPLC (Method A): Ret, 4.26 min; ESI⁺-MS m/z, 382.2 (M+H).

This method was used for the preparation of Ex 8-22 using suitable starting materials:

| EX | Structure | Chemical name | Method | Ret (min) | MS |
|---|---|---|---|---|---|
| 8 | 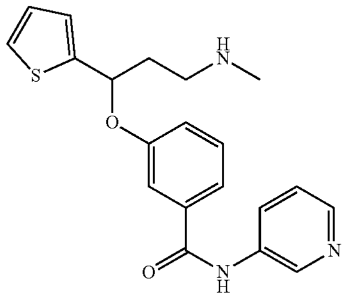 [SMILES: CNCCC(Oc1cccc(C(=O)Nc2cccnc2)c1)c1cccs1] | 3-(3-(Methylamino)-1-(thiophen-2-yl)propoxy)-N-(pyridin-3-yl)benzamide | A | 4.40 | 368.1 (M + H) |
| 9 | 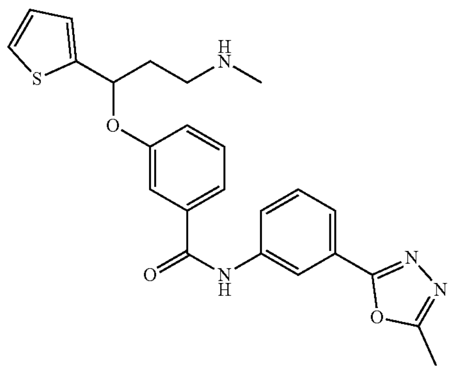 [SMILES: CNCCC(Oc1cccc(C(=O)Nc2cccc(-c3nnc(C)o3)c2)c1)c1cccs1] | N-(3-(5-methyl-1,3,4-oxadiazol-2-yl)phenyl)-3-(3-(methylamino)-1-(thiophen-2-yl)propoxy)benzamide | A | 5.63 | 449.2 (M + H) |
| 10 | 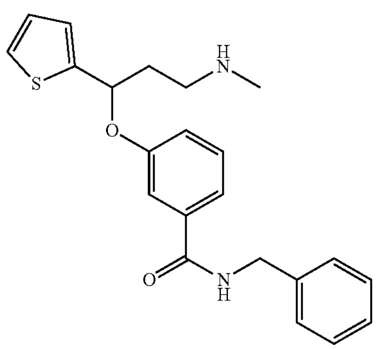 [SMILES: CNCCC(Oc1cccc(C(=O)NCc2ccccc2)c1)c1cccs1] | N-benzyl-3-(3-(methylamino)-1-(thiophen-2-yl)propoxy)benzamide | A | 5.72 | 381.1 (M + H) |
| 11 | 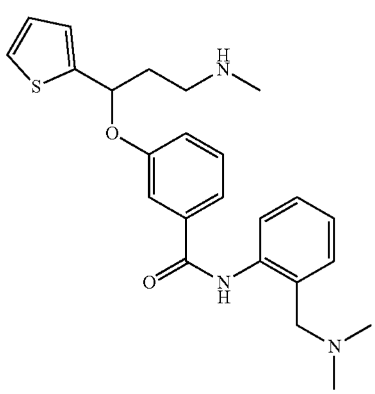 [SMILES: CNCCC(Oc1cccc(C(=O)Nc2ccccc2CN(C)C)c1)c1cccs1] | N-(2-(dimethylamino)methyl)phenyl)-3-(3-(methylamino)-1-(thiophen-2-yl)propoxy)benzamide | A | 4.53 | 424.2 (M + H) |

-continued

| EX | Structure | Chemical name | Method | Ret (min) | MS |
|---|---|---|---|---|---|
| 12 | 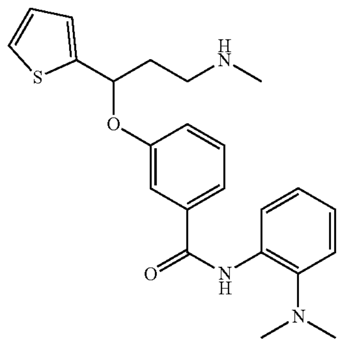 [SMILES: CNCCC(Oc1cccc(C(=O)Nc2ccccc2N(C)C)c1)c1cccs1] | N-(2-(dimethylamino)phenyl)-3-(3-(methylamino)-1-(thiophen-2-yl)propoxy)benzamide | A | 4.96 | 410.2 (M + H) |
| 13 | 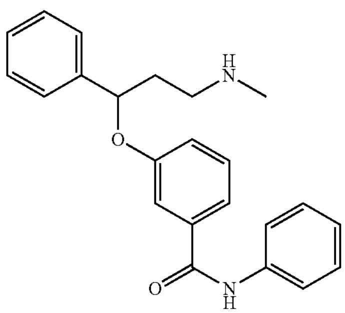 [SMILES: CNCCC(Oc1cccc(C(=O)Nc2ccccc2)c1)c1ccccc1] | 3-(3-(Methylamino)-1-phenylpropoxy)-N-phenylbenzamide | A | 5.94 | 361.1 (M + H) |
| 14 | 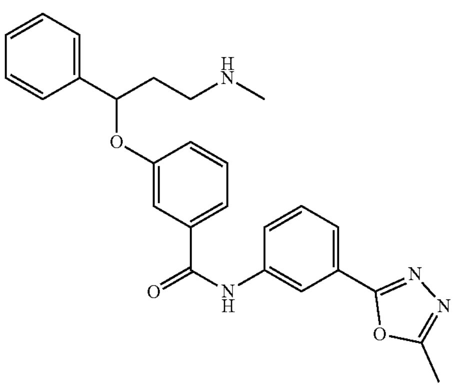 [SMILES: CNCCC(Oc1cccc(C(=O)Nc2cccc(-c3nnc(C)o3)c2)c1)c1ccccc1] | N-(3-(5-methyl-1,3,4-oxadiazol-2-yl)phenyl)-3-(3-(methylamino)-1-phenylpropoxy)benzamide | A | 5.74 | 443.2 (M + H) |
| 15 | 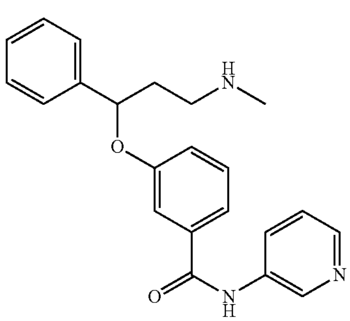 [SMILES: CNCCC(Oc1cccc(C(=O)Nc2cccnc2)c1)c1ccccc1] | 3-(3-(Methylamino)-1-phenylpropoxy)-N-(pyridin-3-yl)benzamide | A | 4.54 | 362.1 (M + H) |

| EX | Structure | Chemical name | Method | Ret (min) | MS |
|---|---|---|---|---|---|
| 16 | 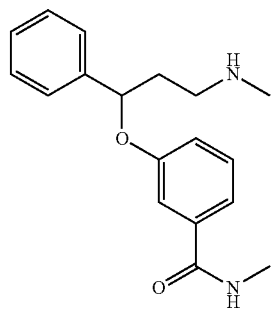 [SMILES: CNCCC(Oc1cccc(C(=O)NC)c1)c1ccccc1] | N-methyl-3-(3-(methylamino)-1-phenylpropoxy)benzamide | A | 4.88 | 299.1 (M + H) |
| 17 | 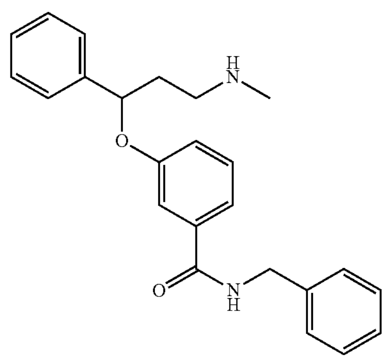 [SMILES: CNCCC(Oc1cccc(C(=O)NCc2ccccc2)c1)c1ccccc1] | N-benzyl-3-(3-(methylamino)-1-phenylpropoxy)benzamide | A | 5.81 | 375.2 (M + H) |
| 18 | 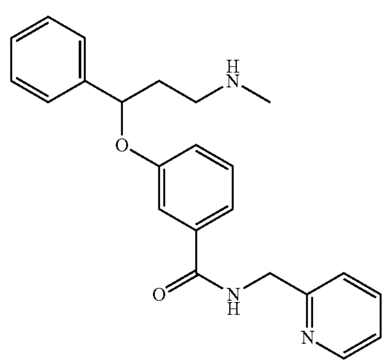 [SMILES: CNCCC(Oc1cccc(C(=O)NCc2ccccn2)c1)c1ccccc1] | 3-(3-(Methylamino)-1-phenylpropoxy)-N-(pyridin-2-ylmethyl)benzamide | A | 4.44 | 376.2 (M + H) |
| 19 | 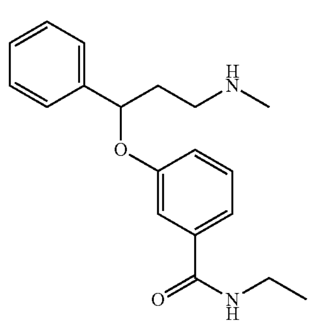 [SMILES: CCNC(=O)c1cccc(OC(CCNC)c2ccccc2)c1] | N-ethyl-3-(3-(methylamino)-1-phenylpropoxy)benzamide | A | 5.10 | 313.1 (M + H) |

| EX | Structure | Chemical name | Method | Ret (min) | MS |
|---|---|---|---|---|---|
| 20 | 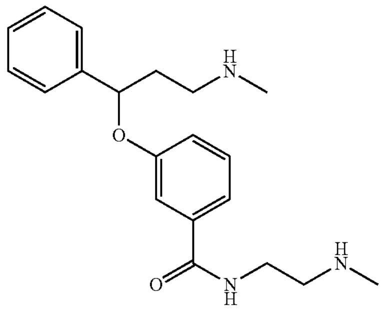 [SMILES: CNCCNC(=O)c1cccc(OC(CCNC)c2ccccc2)c1] | 3-(3-(Methylamino)-1-phenylpropoxy)-N-(2-(methylamino)ethyl)benzamide | A | 4.25 | 342.2 (M + H) |
| 21 | 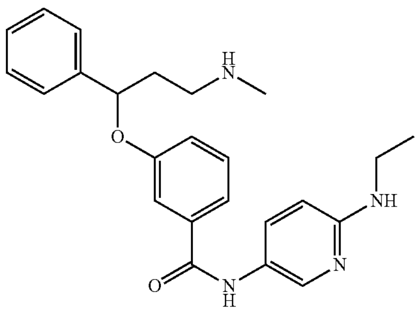 [SMILES: CCNc1ccc(NC(=O)c2cccc(OC(CCNC)c3ccccc3)c2)cn1] | N-(6-(ethylamino)pyridin-3-yl)-3-(3-(methylamino)-1-phenylpropoxy)benzamide | A | 4.66 | 405.3 (M + H) |
| 22 | 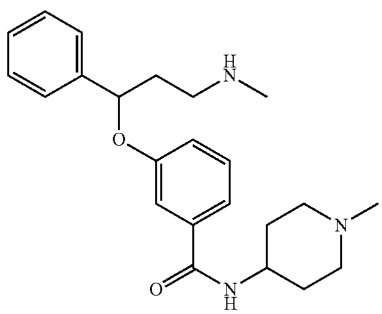 [SMILES: CNCCC(Oc1cccc(C(=O)NC2CCN(C)CC2)c1)c1ccccc1] | 3-(3-(Methylamino)-1-phenylpropoxy)-N-(1-methylpiperidin-4-yl)benzamide | A | 4.30 | 382.2 (M + H) |

Example 23: N-methyl-N-(3-(3-(methylamino)-1-phenylpropoxy)phenyl) benzamide

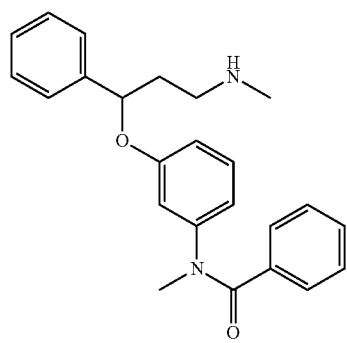 [SMILES: CNCCC(Oc1cccc(N(C)C(=O)c2ccccc2)c1)c1ccccc1]

a) tert-Butyl methyl(3-(3-(methylamino)phenoxy)-3-phenylpropyl)carbamate

A mixture of tert-butyl (3-(3-iodophenoxy)-3-phenylpropyl)(methyl)carbamate (466 mg, 0.99 mmol), methylamine (40% solution in water, 2.57 mL, 30 mmol) and copper powder (32 mg, 0.5 mmol) was heated at 100° C. in a sealed tube for 4 days. The reaction mixture was cooled at rt, DCM was added and washed with NH$_4$Cl solution and brine, dried with Na$_2$SO$_4$, filtered and concentrated. Purification by flash chromatography, silica gel, gradient Hex to 100% EtOAc afford the title compound (264 mg, 71% yield). ESI$^+$-MS m/z, 393.2 (M+Na).

b) tert-Butyl methyl(3-(3-(N-methylbenzamido)phenoxy)-3-phenylpropyl) carbamate

To a solution of the compound obtained in step a (66 mg, 0.17 mmol) in DCM (2 mL), TEA (22 mg, 0.21 mmol) and benzoyl chloride (25 mg, 0.178 mmol) were added and the reaction mixture was stirred at rt for 16 h. Water was added, extracted with DCM, dried with Na$_2$SO$_4$, filtered and concentrated. Purification by flash chromatography, silica gel, gradient Hex to 100% EtOAc afford the title compound (83 mg, 98% yield). ESI$^+$-MS m/z, 497.2 (M+H).

c) Title Compound

To a solution of the compound obtained in step b (83 mg, 0.17 mmol) in dioxane (0.2 mL) at 0° C., HCl (4M solution in dioxane, 0.262 mL, 1.05 mmol) was added and the mixture was stirred at rt for 16 h. The reaction mixture was concentrated to dryness under vacuum. DCM was added, washed with NaHCO$_3$ 10% aq solution and concentrated. Purification by flash chromatography, silica gel, gradient DCM to 40% MeOH, afforded the title compound (30 mg, 46% yield). HPLC (Method A): Ret, 5.67 min; ESI$^+$-MS m/z, 375.2 (M+H).

This method was used for the preparation of Ex 24-38 using suitable starting materials:

| EX | Structure | Chemical name | Method | Ret (min) | MS |
|---|---|---|---|---|---|
| 24 | 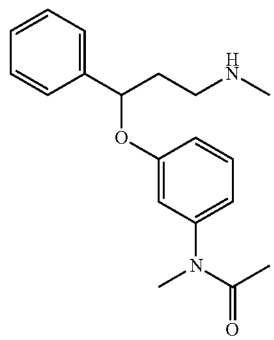 [SMILES: CNCCC(Oc1cccc(N(C)C(C)=O)c1)c1ccccc1] | N-methyl-N-(3-(3-(methylamino)-1-phenylpropoxy)phenyl) acetamide | A | 5.12 | |
| 25 | 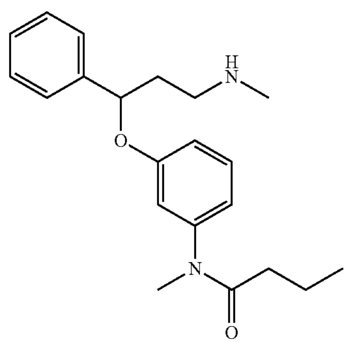 [SMILES: CCCC(=O)N(C)c1cccc(OC(CCNC)c2ccccc2)c1] | N-methyl-N-(3-(3-(methylamino)-1-phenylpropoxy)phenyl) butyramide | A | 5.56 | 341.2 (M + H) |
| 26 | 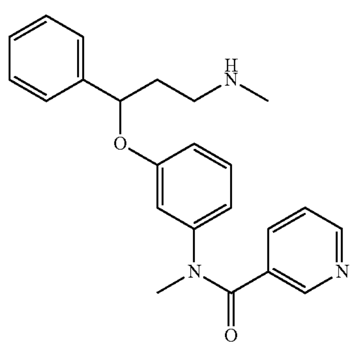 [SMILES: CNCCC(Oc1cccc(N(C)C(=O)c2cccnc2)c1)c1ccccc1] | N-methyl-N-(3-(3-(methylamino)-1-phenylpropoxy)phenyl) nicotinamide | A | 5.05 | |
| 27 | 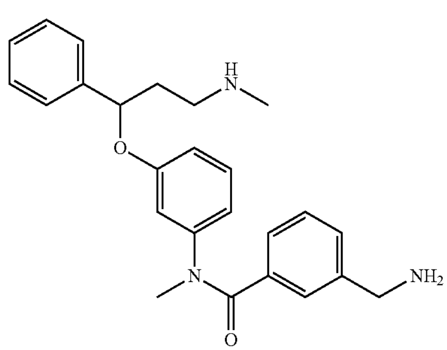 [SMILES: CNCCC(Oc1cccc(N(C)C(=O)c2cccc(CN)c2)c1)c1ccccc1] | 3-(Aminomethyl)-N-methyl-N-(3-(3-(methylamino)-1-phenylpropoxy)phenyl) benzamide | A | 4.51 | 404.2 (M + H) |

| EX | Structure | Chemical name | Method | Ret (min) | MS |
|---|---|---|---|---|---|
| 28 | 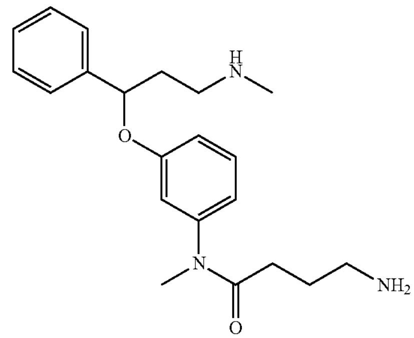 [SMILES: CNCCC(Oc1cccc(N(C)C(=O)CCCN)c1)c1ccccc1] | 4-Amino-N-methyl-N-(3-(3-(methylamino)-1-phenylpropoxy)phenyl)butanamide | A | 4.37 | 356.2 (M + H) |
| 29 | 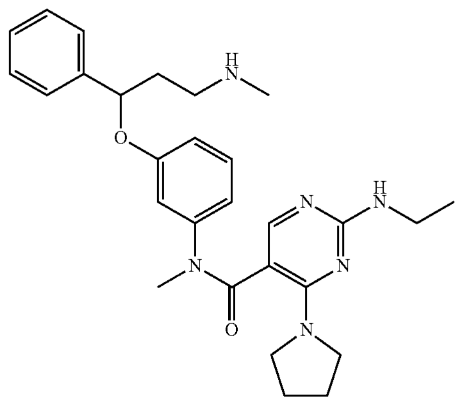 [SMILES: CCNc1ncc(C(=O)N(C)c2cccc(OC(CCNC)c3ccccc3)c2)c(N2CCCC2)n1] | 2-(Ethylamino)-N-methyl-N-(3-(3-(methylamino)-1-phenylpropoxy)phenyl)-4-(pyrrolidin-1-yl)pyrimidine-5-carboxamide | A | 5.13 | 489.3 (M + H) |
| 30 | 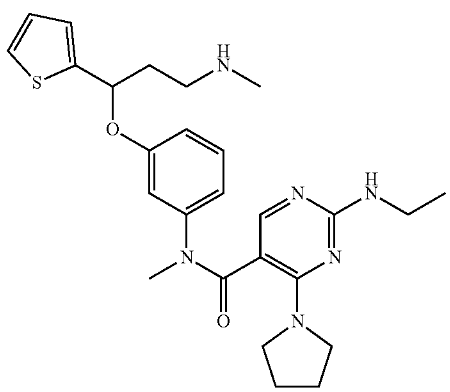 [SMILES: CCNc1ncc(C(=O)N(C)c2cccc(OC(CCNC)c3cccs3)c2)c(N2CCCC2)n1] | 2-(Ethylamino)-N-methyl-N-(3-(3-(methylamino)-1-(thiophen-2-yl)propoxy)phenyl)-4-(pyrrolidin-1-yl)pyrimidine-5-carboxamide | A | 4.99 | 495.3 (M + H) |
| 31 | 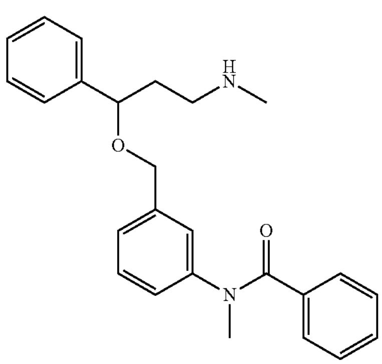 [SMILES: CNCCC(OCc1cccc(N(C)C(=O)c2ccccc2)c1)c1ccccc1] | N-methyl-N-(3-((3-(methylamino)-1-phenylpropoxy)methyl)phenyl)benzamide | A | 5.91 | 389.2 (M + H) |

| EX | Structure | Chemical name | Method | Ret (min) | MS |
|---|---|---|---|---|---|
| 32 | 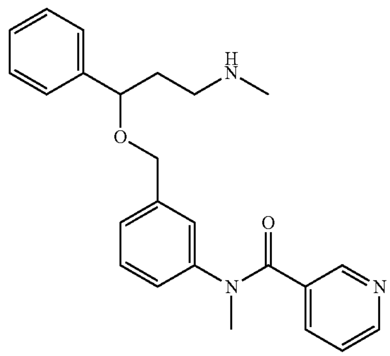 [SMILES: CNCCC(OCc1cccc(N(C)C(=O)c2cccnc2)c1)c1ccccc1] | N-methyl-N-(3-((3-(methylamino)-1-phenylpropoxy)methyl)phenyl)nicotinamide | A | 5.05 | 390.2 (M + H) |
| 33 | 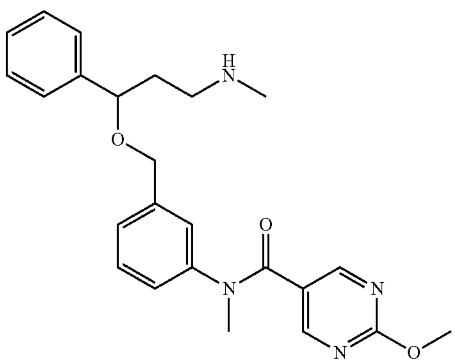 [SMILES: CNCCC(OCc1cccc(N(C)C(=O)c2cnc(OC)nc2)c1)c1ccccc1] | 2-Methoxy-N-methyl-N-(3-((3-(methylamino)-1-phenylpropoxy)methyl)phenyl)pyrimidine-5-carboxamide | A | 5.46 | 421.2 (M + H) |
| 34 | 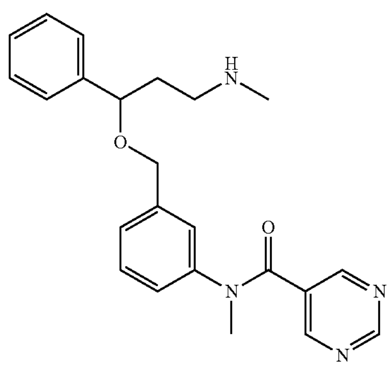 [SMILES: CNCCC(OCc1cccc(N(C)C(=O)c2cncnc2)c1)c1ccccc1] | N-methyl-N-(3-((3-(methylamino)-1-phenylpropoxy)methyl)phenyl)pyrimidine-5-carboxamide | A | 5.31 | 391.2 (M + H) |
| 35 | 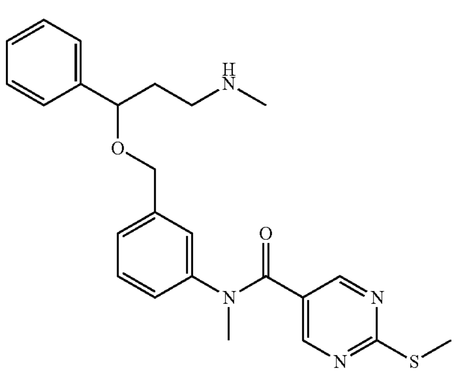 [SMILES: CNCCC(OCc1cccc(N(C)C(=O)c2cnc(SC)nc2)c1)c1ccccc1] | N-methyl-N-(3-((3-(methylamino)-1-phenylpropoxy)methyl)phenyl)-2-(methylthio)pyrimidine-5-carboxamide | A | 5.86 | 437.2 (M + H) |

-continued

| EX | Structure | Chemical name | Method | Ret (min) | MS |
|---|---|---|---|---|---|
| 36 | 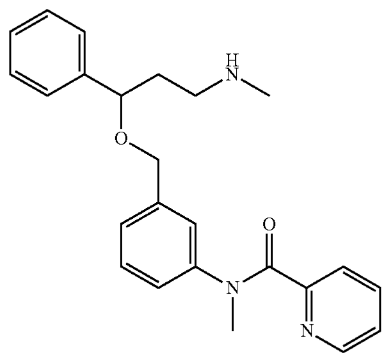 [SMILES: CNCCC(OCc1cccc(N(C)C(=O)c2ccccn2)c1)c1ccccc1] | N-methyl-N-(3-((3-(methylamino)-1-phenylpropoxy)methyl)phenyl)picolinamide | A | 5.33 | 390.2 (M + H) |
| 37 | 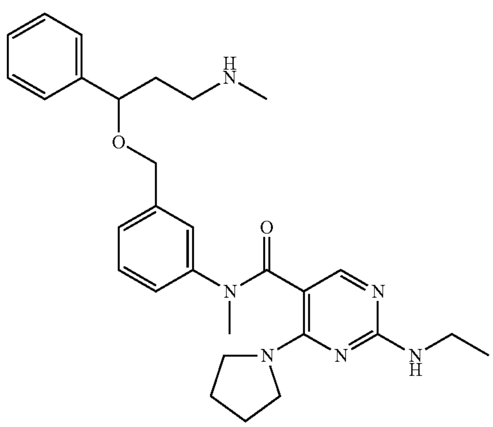 [SMILES: CCNc1ncc(C(=O)N(C)c2cccc(COC(CCNC)c3ccccc3)c2)c(N2CCCC2)n1] | 2-(Ethylamino)-N-methyl-N-(3-((3-(methylamino)-1-phenylpropoxy)methyl)phenyl)-4-(pyrrolidin-1-yl)pyrimidine-5-carboxamide | A | 5.30 | 503.3 (M + H) |
| 38 | 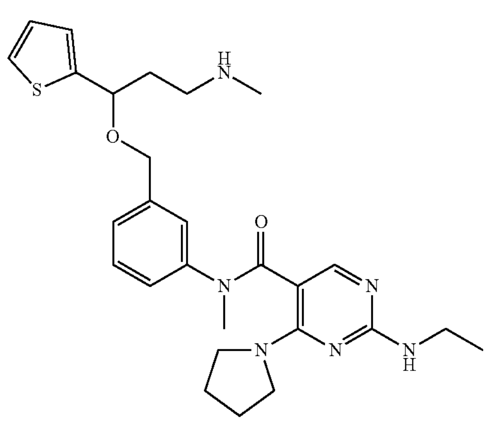 [SMILES: CCNc1ncc(C(=O)N(C)c2cccc(COC(CCNC)c3cccs3)c2)c(N2CCCC2)n1] | 2-(Ethylamino)-N-methyl-N-(3-((3-(methylamino)-1-(thiophen-2-yl)propoxy)methyl)phenyl)-4-(pyrrolidin-1-yl)pyrimidine-5-carboxamide | A | 5.14 | 509.3 (M + H) |

Example 39: N-(3-((3-(methylamino)-1-phenyl-propoxy)methyl)phenyl)benzamide

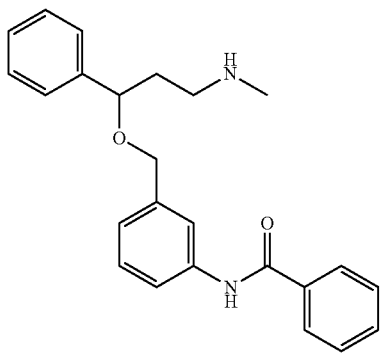 [SMILES: CNCCC(OCc1cccc(NC(=O)c2ccccc2)c1)c1ccccc1]

a) tert-Butyl methyl(3-((3-nitrobenzyl)oxy)-3-phenyl propyl)carbamate

To a solution of tert-butyl (3-hydroxy-3-phenylpropyl)(methyl)carbamate (400 mg, 1.50 mmol) in DMF (4 mL) cooled at 0° C., NaH (90 mg, 60% suspension in mineral oil, 3.77 mmol) was added and the solution was stirred at rt for 30 min. Then, the reaction mixture was cooled again at 0° C. and a solution of 1-(bromomethyl)-3-nitrobenzene (488 mg, 2.26 mmol) and TBAI (278 mg, 0.75 mmol) in DMF (4 mL) was added. The reaction mixture was stirred at rt for 16 h, water was added carefully and extracted with EtOAc; the organic phase was dried with $Na_2SO_4$ and the solvent was removed under vacuum. Purification by flash chromatography, silica gel, gradient from CH to 100% EtOAc afforded the title compound (522 mg, 86% yield). $ESI^+$-MS m/z, 423.1 (M+Na).

b) tert-Butyl (3-((3-aminobenzyl)oxy)-3-phenylpropyl)(methyl)carbamate

To a mixture of the compound obtained in step a (522 mg, 1.30 mmol) and iron powder (728 mg, 13.0 mmol) in EtOH (80% in water, 16 mL), $NH_4Cl$ (35 mg, 0.65 mmol) was added and the mixture was refluxed for 4.5 h. The reaction mixture was cooled at rt, filtered through a plug of celite, rinsed with EtOAc and MeOH and concentrated. Purification by flash chromatography, silica gel, gradient from CH to 100% EtOAc afforded the title compound (480 mg, quant yield). $ESI^+$-MS m/z, 371.2 (M+H).

c) tert-Butyl (3-((3-benzamidobenzyl)oxy)-3-phenyl propyl)(methyl)carbamate

To a solution of the compound obtained in step b (50 mg, 0.13 mmol) cooled at 0° C., TEA (17 mg, 0.16 mmol) and benzoyl chloride (21 mg, 0.15 mmol) were added and the mixture was stirred at rt for 16 h. Water and $NH_4Cl$ sat solution were added, the mixture extracted with EtOAc and the organic phase concentrated under vacuum. Purification by flash chromatography, silica gel, gradient from CH to 100% EtOAc afforded the title compound (63 mg, 98% yield). HPLC (Method A): Ret, 9.01 min; $ESI^-$-MS m/z, 473.2 (M−H).

d) Title Compound

The compound obtained in step c was treated in the conditions used in Ex 23 step c to afford the title compound (78% yield). HPLC (Method A): Ret, 6.15 min; $ESI^+$-MS m/z, 375.2 (M+H).

This method was used for the preparation of Ex 40-51 using suitable starting materials:

| EX | Structure | Chemical name | Method | Ret (min) | MS |
| --- | --- | --- | --- | --- | --- |
| 40 | 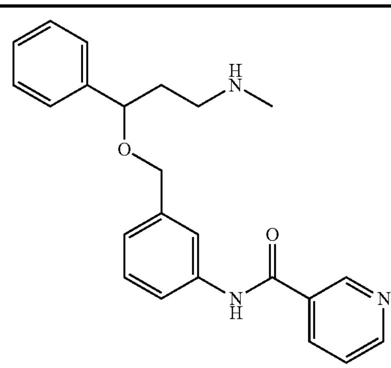 | N-(3-((3-(methylamino)-1-phenylpropoxy)methyl)phenyl)nicotinamide | A | 5.10 | 376.2 (M + H) |
| 41 | 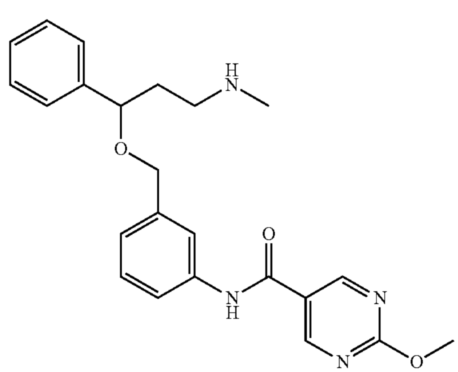 [SMILES: CNCCC(OCc1cccc(NC(=O)c2cnc(OC)nc2)c1)c1ccccc1] | 2-Methoxy-N-(3-((3-(methylamino)-1-phenylpropoxy)methyl)phenyl)pyrimidine-5-carboxamide | A | 5.65 | 407.2 (M + H) |

| EX | Structure | Chemical name | Method | Ret (min) | MS |
|---|---|---|---|---|---|
| 42 | 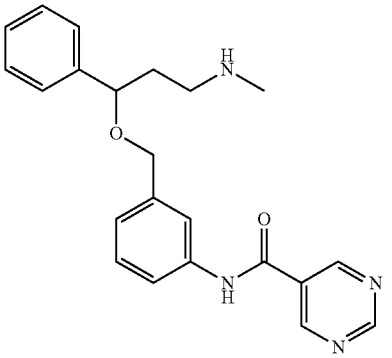 [SMILES: CNCCC(OCc1cccc(NC(=O)c2cncnc2)c1)c1ccccc1] | N-(3-((3-(methylamino)-1-phenylpropoxy)methyl)phenyl)pyrimidine-5-carboxamide | A | 5.35 | 377.1 (M + H) |
| 43 | 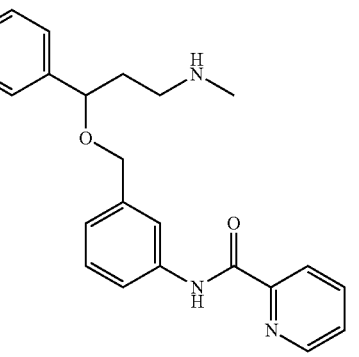 | N-(3-((3-(methylamino)-1-phenylpropoxy)methyl)phenyl)picolinamide | A | 6.18 | 376.2 (M + H) |
| 44 | 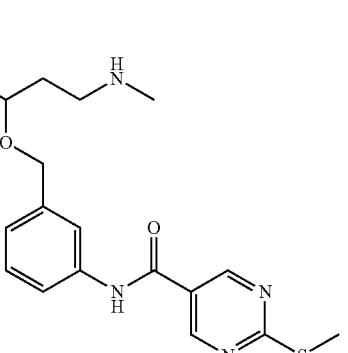 | N-(3-((3-(methylamino)-1-phenylpropoxy)methyl)phenyl)-2-(methylthio)pyrimidine-5-carboxamide | A | 6.05 | 423.2 (M + H) |
| 45 | 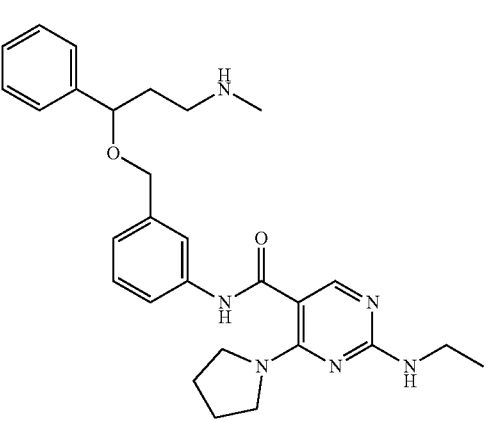 [SMILES: CCNc1ncc(C(=O)Nc2cccc(COC(CCNC)c3ccccc3)c2)c(N2CCCC2)n1] | 2-(Ethylamino)-N-(3-((3-(methylamino)-1-phenylpropoxy)methyl)phenyl)-4-(pyrrolidin-1-yl)pyrimidine-5-carboxamide | A | 5.46 | 489.2 (M + H) |

| EX | Structure | Chemical name | Method | Ret (min) | MS |
|----|-----------|---------------|--------|-----------|-----|
| 46 | 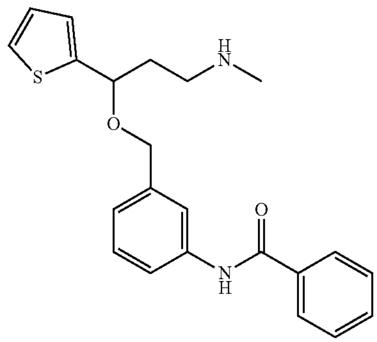 [SMILES: CNCCC(OCc1cccc(NC(=O)c2ccccc2)c1)c1cccs1] | N-(3-((3-(methylamino)-1-(thiophen-2-yl)propoxy)methyl)phenyl)benzamide | A | 6.02 | 381.2 (M + H) |
| 47 | 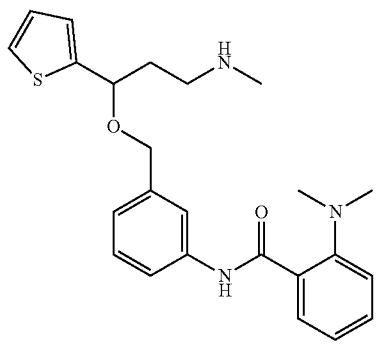 [SMILES: CNCCC(OCc1cccc(NC(=O)c2ccccc2N(C)C)c1)c1cccs1] | 2-(Dimethylamino)-N-(3-((3-(methylamino)-1-(thiophen-2-yl)propoxy)methyl)phenyl)benzamide | A | 5.27 | 424.2 (M + H) |
| 48 | 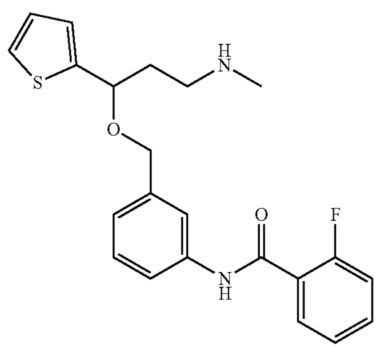 [SMILES: CNCCC(OCc1cccc(NC(=O)c2ccccc2F)c1)c1cccs1] | 2-Fluoro-N-(3-((3-(methylamino)-1-(thiophen-2-yl)propoxy)methyl)phenyl)benzamide | A | 6.05 | 399.1 (M + H) |
| 49 | 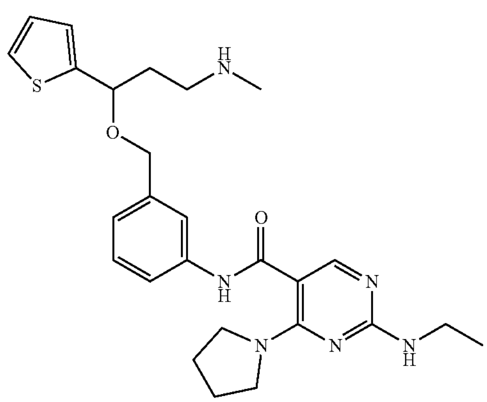 [SMILES: CCNc1ncc(C(=O)Nc2cccc(COC(CCNC)c3cccs3)c2)c(N2CCCC2)n1] | 2-(Ethylamino)-N-(3-((3-(methylamino)-1-(thiophen-2-yl)propoxy)methyl)phenyl)-4-(pyrrolidin-1-yl)pyrimidine-5-carboxamide | A | 5.31 | 495.2 (M + H) |

| EX | Structure | Chemical name | Method | Ret (min) | MS |
|---|---|---|---|---|---|
| 50 | 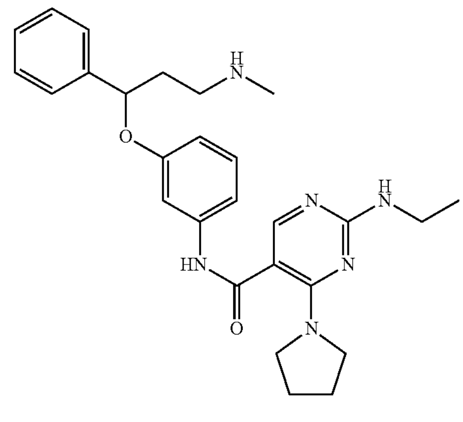 [SMILES: CCNc1ncc(C(=O)Nc2cccc(OC(CCNC)c3ccccc3)c2)c(N2CCCC2)n1] | 2-(Ethylamino)-N-(3-(3-(methylamino)-1-phenylpropoxy)phenyl)-4-(pyrrolidin-1-yl)pyrimidine-5-carboxamide | A | 5.29 | 475.3 (M + H) |
| 51 | 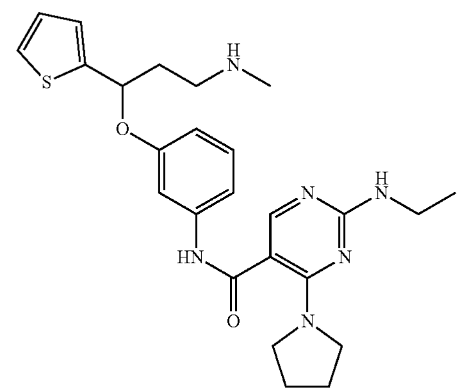 [SMILES: CCNc1ncc(C(=O)Nc2cccc(OC(CCNC)c3cccs3)c2)c(N2CCCC2)n1] | 2-(Ethylamino)-N-(3-(3-(methylamino)-1-(thiophen-2-yl)propoxy)phenyl)-4-(pyrrolidin-1-yl)pyrimidine-5-carboxamide | A | 5.16 | 481.2 (M + H) |

Example 52: N-benzyl-3-((3-(methylamino)-1-phenylpropoxy)methyl)aniline

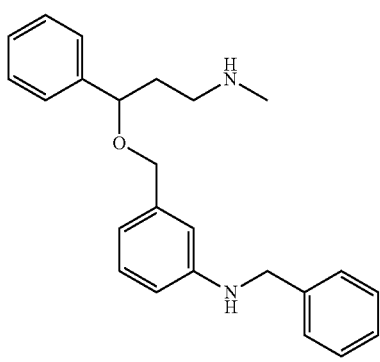 [SMILES: CNCCC(OCc1cccc(NCc2ccccc2)c1)c1ccccc1]

a) tert-Butyl (3-((3-(benzylamino)benzyl)oxy)-3-phenylpropyl)(methyl)carbamate

To a solution of the compound obtained in Ex 39 step b (132 mg, 0.35 mmol) in dry THF (1 mL) under Ar atmosphere, benzaldehyde (38 mg, 0.35 mmol) was added and the reaction mixture was stirred at rt for 35 min. The reaction mixture was concentrated to dryness under vacuum, the residue was dissolved in MeOH (3 mL), NaBH$_4$ (27 mg, 0.71 mmol) was added and the mixture was stirred at rt for 3 h. The reaction mixture was concentrated. Purification by flash chromatography, silica gel, gradient from Hex to 100% EtOAc afforded the title compound (90 mg, 55% yield). HPLC (Method B): Ret, 9.24; ESI$^+$-MS m/z, 461.2 (M+H).

b) Title Compound

The compound obtained in step a was treated with the conditions used in Ex 23 step c, to afford the title compound (75% yield). HPLC (Method A): Ret, 6.20 min; ESI$^+$-MS m/z, 361.2 (M+H).

This method was used for the preparation of Ex 53 using suitable starting materials:

| EX | Structure | Chemical name | Method | Ret (min) | MS |
|----|-----------|---------------|--------|-----------|-----|
| 53 | 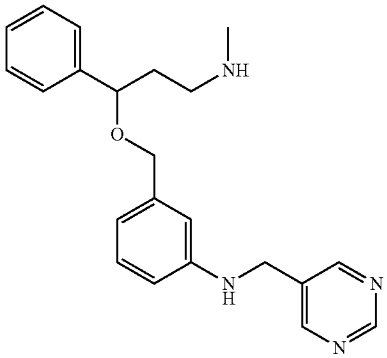 [SMILES: CNCCC(OCc1cccc(NCc2cncnc2)c1)c1ccccc1] | 3-((3-(Methylamino)-1-phenylpropoxy)methyl)-N-(pyrimidin-5-ylmethyl)aniline | A | 5.40 | 363.2 (M + H) |

Example 54: N-(3-((3-(dimethylamino)-1-(thiophen-2-yl)propoxy)methyl)phenyl) benzamide

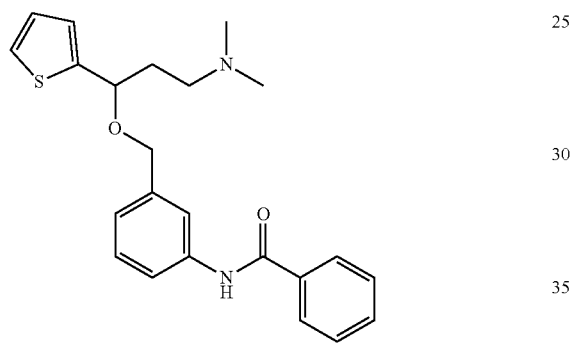

To a solution of Ex 46 (58 mg, 0.15 mmol) in DCE (1.2 mL), DIPEA (30 mg, 0.23 mmol), paraformaldehyde (18 mg, 0.56 mmol) and NaBH(OAc)$_3$ (120 mg, 0.56 mmol) were added and the reaction mixture was stirred at rt for 16 h. NaHCO$_3$ sat solution was added, extracted with DCM and concentrated under vacuum. Purification by flash chromatography, silica gel, gradient from DCM to 20% MeOH afforded the title compound (48 mg, 80% yield). HPLC (Method A): Ret, 6.04 min; ESI⁻-MS m/z, 393.1 (M–H).

This method was used for the preparation of Ex 55 using suitable starting materials:

| EX | Structure | Chemical name | Method | Ret (min) | MS |
|----|-----------|---------------|--------|-----------|-----|
| 55 | 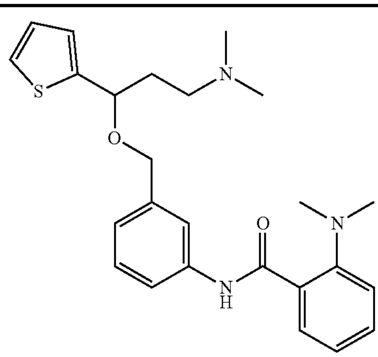 | 2-(Dimethylamino)-N-(3-((3-(dimethylamino)-1-(thiophen-2-yl)propoxy)methyl)phenyl)benzamide | A | 5.38 | 438.2 (M + H) |

Example 56: N-ethyl-N-(3-(3-(methylamino)-1-(thiophen-2-yl)propoxy)benzyl) benzamide

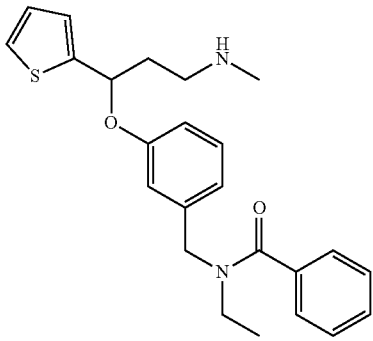 [SMILES: CCN(Cc1cccc(OC(CCNC)c2cccs2)c1)C(=O)c1ccccc1]

a) N-(3-(3-chloro-1-(thiophen-2-yl)propoxy)benzyl) ethanamine

The compound obtained in Ex 1 step a was treated with ethylamine in the conditions used in Ex 1 step b to afford the title compound (91% yield). HPLC (Method B): Ret, 4.01 min; ESI$^+$-MS m/z, 310.1 (M+H).

b) N-(3-(3-chloro-1-(thiophen-2-yl)propoxy)benzyl)-N-ethylbenzamide

To a solution of the compound obtained in step a (80 mg, 0.26 mmol) in DCM (2 mL), TEA (52 mg, 0.51 mmol) and benzoyl chloride (54 mg, 0.38 mL) were added and the mixture was stirred at rt for 3 h. DCM was added and the mixture was washed with water and brine. The organic phase was dried over MgSO$_4$ and concentrated under vacuum. Purification by flash chromatography, silica gel, gradient from CH to 100% MeOH afforded the title compound (758 mg, 70% yield). HPLC (Method B): Ret, 5.89 min; ESI$^+$-MS m/z, 414.1 (M+H).

c) Title Compound

The compound obtained in step b was treated in the conditions used in Ex 1 step c to afford the title compound (33% yield). HPLC (Method A): Ret, 5.97 min; ESI$^+$-MS m/z, 409.2 (M+H).

Example 57: N-benzyl-N-(3-((3-(methylamino)-1-phenylpropoxy)methyl)phenyl) acetamide

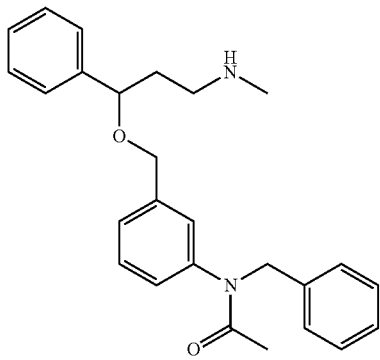 [SMILES: CNCCC(OCc1cccc(N(Cc2ccccc2)C(C)=O)c1)c1ccccc1]

a) tert-Butyl (3-((3-(N-benzylacetamido)benzyl)oxy)-3-phenyl propyl)(methyl) carbamate To a solution of the compound obtained in Ex 52 step a (75 mg, 0.16 mmol) in DCM (0.7 mL) cooled at 0° C., acetic anhydride (8.4 mg, 0.08 mmol) was added and the mixture was stirred at rt for 16 h. DCM was added and after washing with NaHCO$_3$ sat solution, it was concentrated under vacuum. Purification by flash chromatography, silica gel, gradient from Hex to 100% EtOAc afforded the title compound (51 mg, 62% yield). HPLC (Method A): Ret, 9.21 min; ESI$^+$-MS m/z, 525.2 (M+Na).

b) Title Compound

The compound obtained in step a was treated in the conditions used in Ex 23 step c to afford the title compound (83% yield). HPLC (Method A): Ret, 6.13 min; ESI$^+$-MS m/z, 403.2 (M+H).

Example 58: 3-((3-(Methylamino)-1-phenylpropoxy)methyl)-N-phenylaniline

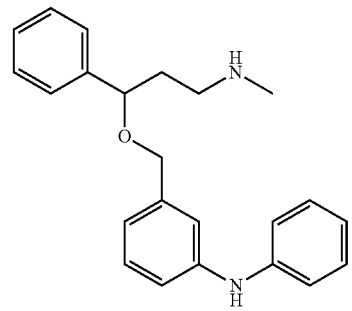 [SMILES: CNCCC(OCc1cccc(Nc2ccccc2)c1)c1ccccc1]

a) tert-Butyl methyl(3-phenyl-3-((3-(phenylamino)benzyl)oxy)propyl)carbamate A sealed tube was charged with tert-butyl (3-((3-iodobenzyl)oxy)-3-phenylpropyl)(methyl) carbamate (200 mg, 0.41 mmol), K$_2$CO$_3$ (115 mg, 0.83 mmol), CuI (16 mg, 0.084 mmol) and L-proline (20 mg, 0.16 mmol) under Ar atmosphere. A solution of aniline (58 mg, 0.62 mmol) in dry DMSO (0.25 mL) was added and the mixture was heated at 90° C. for 23 h. The reaction mixture was cooled at rt, DCM was added and washed with water and NH$_4$Cl sat solution and the organic layer was concentrated under vacuum. Purification by flash chromatography, silica gel, gradient from Hex to 100% EtOAc afforded the title compound (56 mg, 30% yield). HPLC (Method A): Ret, 9.66 min; ESI$^+$-MS m/z, 469.2 (M+Na).

b) Title Compound

The compound obtained in step a was treated in the conditions used in Ex 23 step c to afford the title compound (quant yield). HPLC (Method A): Ret, 6.64 min; ESI$^+$-MS m/z, 347.2 (M+H).

This method was used for the preparation of Ex 59 using suitable starting materials:

| EX | Structure | Chemical name | Method | Ret (min) | MS |
|---|---|---|---|---|---|
| 59 | 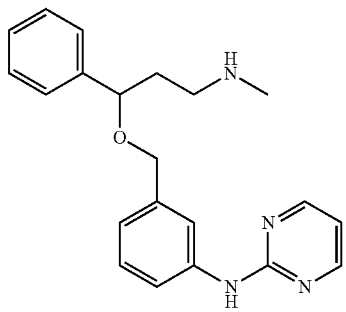 [SMILES: CNCCC(OCc1cccc(Nc2ncccn2)c1)c1ccccc1] | N-(3-((3-(methylamino)-1-phenylpropoxy)methyl)phenyl)pyrimidin-2-amine | A | 5.68 | 349.2 (M + H) |

Example 60: 2-(Ethylamino)-N-methyl-N-(3-(3-(methylamino)-1-phenylpropoxy) phenyl)pyrimidine-5-carboxamide

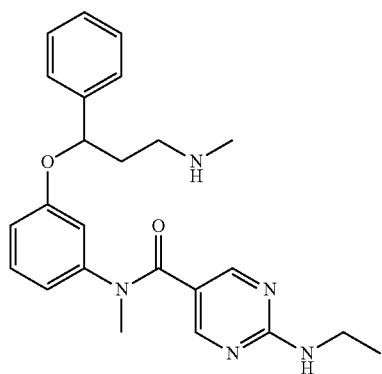 [SMILES: CCNc1ncc(C(=O)N(C)c2cccc(OC(CCNC)c3ccccc3)c2)cn1]

a) tert-Butyl (3-(3-(2-(ethylamino)-N-methylpyrimidine-5-carboxamido)phenoxy)-3-phenylpropyl)(methyl)carbamate To a solution of tert-butyl (3-(3-iodophenoxy)-3-phenylpropyl)(methyl)carbamate (50 mg, 0.27 mmol) in dioxane (3 mL), CuI (16 mg, 0.08 mmol), $K_3PO_4$ (118 mg, 0.55 mmol) and N1,N2-dimethylethane-1,2-diamine (7.4 mg, 0.08 mmol) were added and the mixture was heated at 100° C. under Ar atmosphere for 20 h. The reaction mixture was cooled to rt and the solvent was removed under vacuum. Purification by flash chromatography, silica gel, gradient DCM to 25% MeOH afforded the title compound (51 mg, 35% yield). HPLC (Method A): Ret, 8.48 min; $ESI^+$-MS m/z, 542.2 (M+Na).

b) Title Compound

The compound obtained in step a was treated in the conditions used in Ex 23 step c to afford the title compound (quant yield). HPLC (Method A): Ret, 5.48 min; $ESI^+$-MS m/z, 420.2 (M+H).

This method was used for the preparation of Ex 61 using suitable starting materials:

| EX | Structure | Chemical name | Method | Ret (min) | MS |
|---|---|---|---|---|---|
| 61 | 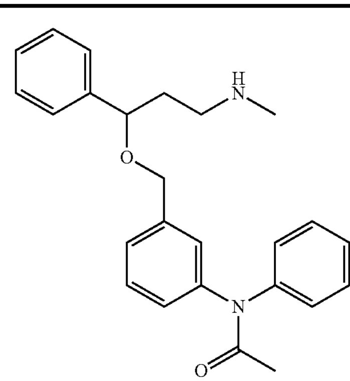 | N-(3-((3-(methylamino)-1-phenylpropoxy)methyl)phenyl)-N-phenylacetamide | A | 5.97 | 389.2 (M + H) |

Example 62: N-methyl-N-(3-(3-(methylamino)-1-(thiophen-2-yl)propoxy) phenyl)acetamide

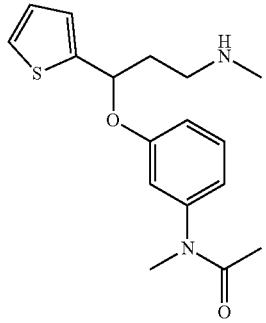 [SMILES: CNCCC(Oc1cccc(N(C)C(C)=O)c1)c1cccs1]

a) 2-(1,3-Dichloropropyl)thiophene

To a mixture of 3-chloro-1-(thiophen-2-yl)propan-1-ol (900 mg, 5.09 mmol) and TEA (1.0 g, 10.18 mmol) in DCM (12 mL) cooled at 0° C., methanesulfonyl chloride (700 mg, 6.11 mmol) was added dropwise and the reaction mixture was stirred at 0° C. for 1 h. Brine was added, and the mixture was extracted with DCM and the organic phase dried with $Na_2SO_4$. The organic phase was concentrated under vacuum to afford the title compound that was used in the next step without further purification.

b) N-(3-(3-chloro-1-(thiophen-2-yl)propoxy)phenyl)-N-methylacetamide

To a solution of N-(3-hydroxyphenyl)-N-methylacetamide (120 mg, 0.72 mmol) in DMF (7 mL) cooled at 0° C., NaH (60% suspension in mineral oil, 35 mg, 0.87 mmol) was added and the mixture was stirred at rt for 30 min. The reaction mixture was cooled again at 0° C. and a solution of the compound obtained in step a (213 mg, 1.09 mmol) in DMF (3 mL) and stirred at rt for 2 h. Water was added and the mixture was extracted with EtOAc. The organic phase was dried with $Na_2SO_4$, filtered and concentrated under vacuum. Purification by flash chromatography, silica gel, gradient CH to 100% EtOAc afforded a mixture of the title compound and alkene elimination product that was used in the next step without further purification.

c) Title Compound

The compound obtained in step b was treated in the conditions used in Ex 1 step c to afford the title compound (73% yield, global three steps). HPLC (Method A): Ret, 4.9 min; ESI$^+$-MS m/z, 319.1 (M+H).

This method was used for the preparation of Ex 63-69 using suitable starting materials:

| EX | Structure | Chemical name | Method | Ret (min) | MS |
|---|---|---|---|---|---|
| 63 | 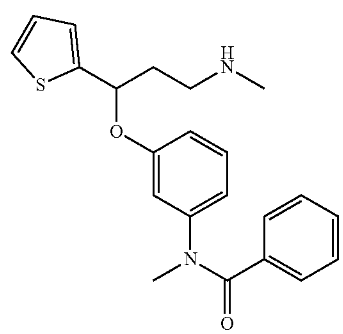 [SMILES: CNCCC(Oc1cccc(N(C)C(=O)c2ccccc2)c1)c1cccs1] | N-methyl-N-(3-(3-(methylamino)-1-(thiophen-2-yl)propoxy)phenyl)benzamide | A | 5.54 | 381.1 (M + H) |
| 64 | 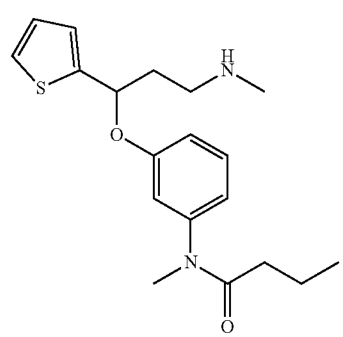 [SMILES: CCCC(=O)N(C)c1cccc(OC(CCNC)c2cccs2)c1] | N-methyl-N-(3-(3-(methylamino)-1-(thiophen-2-yl)propoxy)phenyl)butyramide | A | 5.39 | 347.1 (M + H) |

| EX | Structure | Chemical name | Method | Ret (min) | MS |
|---|---|---|---|---|---|
| 65 | 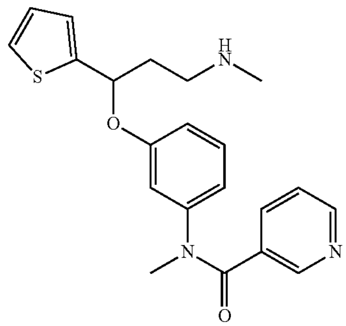 [SMILES: CNCCC(Oc1cccc(N(C)C(=O)c2cccnc2)c1)c1cccs1] | N-methyl-N-(3-(3-(methylamino)-1-(thiophen-2-yl)propoxy)phenyl)nicotinamide | A | 4.91 | 382.1 (M + H) |
| 66 | 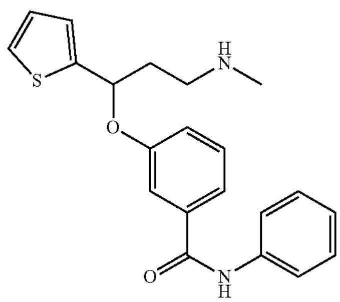 [SMILES: CNCCC(Oc1cccc(C(=O)Nc2ccccc2)c1)c1cccs1] | 3-(3-(Methylamino)-1-(thiophen-2-yl)propoxy)-N-phenylbenzamide | A | 5.84 | 367.1 (M + H) |
| 67 | 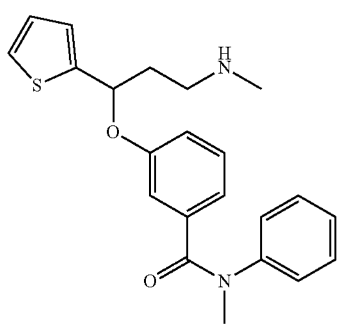 [SMILES: CNCCC(Oc1cccc(C(=O)N(C)c2ccccc2)c1)c1cccs1] | N-methyl-3-(3-(methylamino)-1-(thiophen-2-yl)propoxy)-N-phenylbenzamide | A | 5.74 | 381.1 (M + H) |
| 68 | 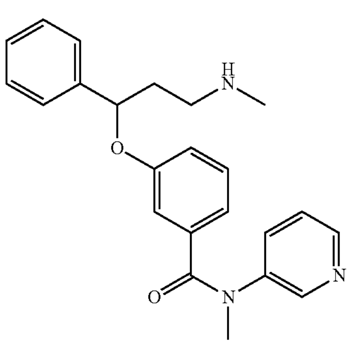 [SMILES: CNCCC(Oc1cccc(C(=O)N(C)c2cccnc2)c1)c1ccccc1] | N-methyl-3-(3-(methylamino)-1-phenylpropoxy)-N-(pyridin-3-yl)benzamide | A | 4.67 | 376.2 (M + H) |

| EX | Structure | Chemical name | Method | Ret (min) | MS |
|---|---|---|---|---|---|
| 69 | 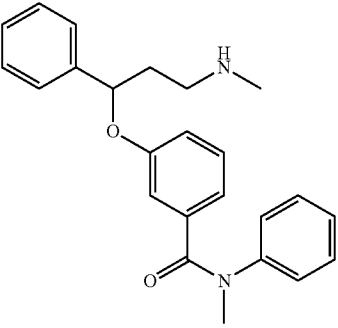 [SMILES: CNCCC(Oc1cccc(C(=O)N(C)c2ccccc2)c1)c1ccccc1] | N-methyl-3-(3-(methylamino)-1-phenylpropoxy)-N-phenylbenzamide | A | 5.85 | 375.2 (M + H) |

Ex 70-71 were prepared by a sequence of reactions according to the method described in Ex 1 using suitable starting materials:

| EX | Structure | Chemical name | Method | Ret (min) | MS |
|---|---|---|---|---|---|
| 70 | 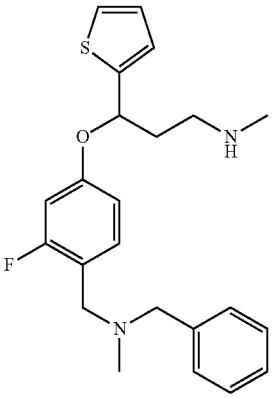 [SMILES: CNCCC(Oc1ccc(CN(C)Cc2ccccc2)c(F)c1)c1cccs1] | 3-(4-((Benzyl(methyl)amino)methyl)-3-fluorophenoxy)-N-methyl-3-(thiophen-2-yl)propan-1-amine | A | 4.85 | 399.2 (M + H) |
| 71 | 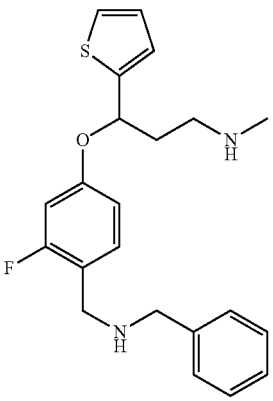 [SMILES: CNCCC(Oc1ccc(CNCc2ccccc2)c(F)c1)c1cccs1] | 3-(4-((Benzylamino)methyl)-3-fluorophenoxy)-N-methyl-3-(thiophen-2-yl)propan-1-amine | A | 4.76 | 385.2 (M + H) |

Examples of Biological Activity

Binding Assay to Human α2δ-1 Subunit of Cav2.2 Calcium Channel.

Human α2δ-1 enriched membranes (2.5 μg) were incubated with 15 nM of radiolabeled [3H]-Gabapentin in assay buffer containing Hepes-KOH 10 mM, pH 7.4.

NSB (non specific binding) was measured by adding 10 μM pregabalin. The binding of the test compound was measured in five different concentrations. After 60 min incubation at 27° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, pH 7.4.

Filter plates were dried at 60° C. for 1 hour and 30 µl of scintillation cocktail were added to each well before radioactivity reading.

Readings were performed in a Trilux 1450 Microbeta radioactive counter (Perkin Elmer).

Binding Assay to Human Norepinephrine Transporter (NET).

Human norepinephrine transporter (NET) enriched membranes (5 µg) were incubated with 5 nM of radiolabeled [3H]-Nisoxetin in assay buffer containing 50 mM Tris-HCl, 120 mM NaCl, 5 mM KCl, pH 7.4.

NSB (non specific binding) was measured by adding 10 µM desipramine. The binding of the test compound was measured in five different concentrations. After 60 min incubation at 4° C., binding reaction was terminated by filtering through Multiscreen GF/C (Millipore) presoaked in 0.5% polyethyleneimine in Vacuum Manifold Station, followed by 3 washes with ice-cold filtration buffer containing 50 mM Tris-HCl, 0.9% NaCl, pH 7.4.

Filter plates were dried at 60° C. for 1 hour and 30 µl of scintillation cocktail were added to each well before radioactivity reading.

Readings were performed in a Trilux 1450 Microbeta radioactive counter (Perkin Elmer).

The following scale has been adopted for representing the binding to the α2δ-1 receptor expressed as Ki:

+Ki-α2δ-1>=3000 nM
++500 nM<Ki-α2δ-1<3000 nM
+++100 nM<Ki-α2δ-1<500 nM
++++Ki-α2δ-1<100 nM

For the dual compounds and regarding the NET receptor, the following scale has been adopted for representing the binding expressed as Ki:

+Ki-NET>=1000 nM
++500 nM<Ki-NET<1000 nM
+++100 nM<Ki-NET<500 nM
++++Ki-NET<100 nM

The results of the binding for α2δ-1 receptor are shown in Table 1:

TABLE 1

| Example number | Ki(nM) alpha2delta Hum |
|---|---|
| 1 | +++ |
| 2 | ++ |
| 3 | +++ |
| 4 | +++ |
| 5 | +++ |
| 6 | +++ |
| 7 | + |
| 8 | ++ |
| 9 | ++ |
| 10 | ++ |
| 11 | ++ |
| 12 | ++ |
| 13 | + |
| 14 | + |
| 15 | + |
| 16 | + |
| 17 | + |
| 18 | + |
| 19 | + |
| 20 | ++ |
| 21 | + |
| 22 | ++ |
| 23 | + |
| 24 | + |
| 25 | + |
| 26 | + |

TABLE 1-continued

| Example number | Ki(nM) alpha2delta Hum |
|---|---|
| 27 | + |
| 28 | + |
| 29 | + |
| 30 | ++ |
| 31 | + |
| 32 | + |
| 33 | + |
| 34 | + |
| 35 | + |
| 36 | + |
| 37 | ++ |
| 38 | ++ |
| 39 | + |
| 40 | + |
| 41 | + |
| 42 | + |
| 43 | + |
| 44 | + |
| 45 | ++ |
| 46 | + |
| 47 | + |
| 48 | + |
| 49 | ++ |
| 50 | + |
| 51 | ++ |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | + |
| 66 | ++ |
| 67 | + |
| 68 | + |
| 69 | + |
| 70 | + |
| 71 | + |

The binding results for the α2δ-1 and the NET receptor for the dual compounds are shown in Table 2:

TABLE 2

| Example number | Ki(nM) NET Hum | Ki(nM) alpha2delta Hum |
|---|---|---|
| 2 | +++ | ++ |
| 6 | ++ | +++ |
| 13 | ++ | + |
| 14 | +++ | + |
| 15 | +++ | + |
| 17 | ++ | + |
| 18 | ++ | + |
| 20 | ++ | ++ |
| 22 | + | ++ |
| 27 | ++ | + |
| 28 | ++ | + |
| 38 | ++ | ++ |
| 39 | ++ | + |
| 41 | ++ | + |
| 43 | ++ | + |
| 46 | ++ | + |
| 48 | ++ | + |
| 50 | ++ | + |
| 58 | +++ | + |

TABLE 2-continued

| Example number | Ki(nM) NET Hum | Ki(nM) alpha2delta Hum |
|---|---|---|
| 70 | +++ | + |
| 71 | ++++ | + |

The invention claimed is:

1. A compound of general formula (I):

$$\text{(I)}$$

wherein:
- $R_1$ and $R'_1$ are independently selected from a hydrogen atom and a branched or unbranched $C_{1-6}$ alkyl radical;
- $R_2$ is 6-membered aryl optionally substituted by a halogen atom, a branched or unbranched $C_{1-6}$-alkyl radical, a branched or unbranched $C_{1-6}$-alkoxy radical, a $C_{1-6}$-haloalcoxy radical, a $C_{1-6}$-haloalkyl radical or a hydroxyl radical; or a substituted or unsubstituted 5 or 6-membered heteroaryl having at least one heteroatom selected from N, O and S;
- n is 1;
- m is 0 or 1;
- W is —$(CH_2)_p$—; —C(O)—; or a bond;
- p is 1 or 2;
- Z is $NR_3R_4$;
- $R_3$ is a hydrogen atom; a branched or unbranched $C_{1-6}$ alkyl radical; a benzyl radical; or a phenyl radical;
- $R_4$ is a branched or unbranched $C_{1-6}$ alkyl radical optionally substituted by a halogen atom, a hydroxyl radical, a branched or unbranched $C_{1-6}$ alkoxy radical or a —$NR_{4a}R_{4b}$ radical; a —$(CH_2)_s$-heteroaryl radical, wherein the heteroaryl group is a 5 or 6-membered ring having at least one nitrogen atom as heteroatom, optionally substituted by a —$NR_{4c}R_{4d}$ radical, and s is 0, 1 or 2; a heterocycloalkyl radical optionally substituted by $R_{4e}$; a —$(CH_2)_r$-aryl radical wherein the aryl group is 6-membered ring optionally substituted by at least one $R_5$ radical, and r is 0, 1 or 2; or a —$C(O)R_5$ radical;
- $R_{4a}$, $R_{4b}$, $R_{4c}$, $R_{4d}$ and $R_{4e}$ are independently selected from the group consisting of a hydrogen atom and a branched or unbranched $C_{1-6}$ alkyl radical;
- $R_5$ is a hydrogen atom; a hydroxyl radical; a branched or unbranched $C_{1-6}$-alkoxy radical; a —$(CH_2)_j$—$NR_{5a}R_{5b}$ radical; a —$NR_{5c}R_{5d}$ radical; or a 5-membered heteroaromatic ring having one or more N and/or O as heteroatoms, optionally substituted by $R_{5e}$;
- $R_{5a}$, $R_{5b}$, $R_{5c}$, $R_{5d}$ and $R_{5e}$ are independently a hydrogen atom or a branched or unbranched $C_{1-6}$ alkyl radical;
- j is 0 or 1;
- $R_6$ is a branched or unbranched $C_{1-6}$ alkyl radical; a —$(CH_2)_q$—$NR_{6a}R_{6b}$ radical; a 5 or 6-membered nitrogen containing heteroaryl ring optionally having at least one additional heteroatom selected from O and N and optionally substituted by at least one $R_7$; or a 6-membered aryl optionally substituted by at least one $R_8$;
- $R_{6a}$ and $R_{6b}$ are independently selected from the group consisting of a hydrogen atom and $C_{1-6}$ alkyl;
- q is 0, 1, 2, 3 or 4;
- $R_7$ is selected from the group consisting of a hydrogen atom, a branched or unbranched $C_{1-6}$-alkoxy radical, a branched or unbranched $C_{1-6}$-alkylthio radical; a —$NR_{7a}R_{7b}$ radical; and a 5-membered heterocycloalkyl ring having at least one heteroatom selected from O, N and S;
- $R_{7a}$ and $R_{7b}$ are independently selected from the group consisting of H and $C_{1-6}$ alkyl;
- $R_8$ is a hydrogen atom, a halogen atom, a branched or unbranched $C_{1-6}$-alkyl radical or a —$(CH_2)_t$—$NR_{8a}R_{8b}$ radical;
- t is 0 or 1;
- $R_{8a}$ and $R_{8b}$ are independently selected from the group consisting of a hydrogen atom and a branched or unbranched $C_{1-6}$ alkyl radical;

or a pharmaceutically acceptable salt, isomer, or solvate thereof.

2. The compound according to claim 1, wherein $R_2$ is a phenyl radical optionally substituted by a halogen atom, a branched or unbranched $C_{1-6}$-alkyl radical, a branched or unbranched $C_{1-6}$-alkoxy radical, a $C_{1-6}$-haloalkoxy radical, a $C_{1-6}$-haloalklyl radical or a hydroxyl radical; or a substituted or unsubstituted thiophene group.

3. The compound according to claim 1, wherein $R_4$ is:
a branched or unbranched $C_{1-6}$ alkyl radical optionally substituted by a —$NR_{4a}R_{4b}$ radical;
a radical selected from:

a radical:

a radical selected from:

or
a —$C(O)R_6$ radical;
wherein $R_{4a}$, $R_{4b}$, $R_{4c}$, $R_{4d}$, $R_{4e}$, $R_5$ and $R_6$ are as defined in claim 1.

4. The compound according to claim 1, wherein $R_5$ is independently selected from the group consisting of a hydrogen atom; a branched or unbranched $C_{1-6}$ alkoxy radical; a —$(CH_2)_j$—$NR_{5a}R_{5b}$ radical; a —$NR_{5c}R_{5d}$ radical and a radical:

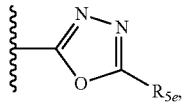

wherein $R_{5a}$, $R_{5b}$, $R_{5c}$, $R_{5d}$, $R_{5e}$ and j are as defined in claim 1.

5. The compound according to claim 1, wherein $R_6$ is independently selected from the group consisting of a branched or unbranched $C_{1-6}$ alkyl radical; a —$(CH_2)_q$—$NR_{6a}R_{6b}$ radical and a radical selected from:

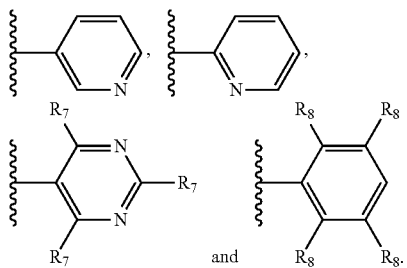

wherein $R_{6a}$, $R_{6b}$, $R_7$, $R_8$ and q are as defined in claim 1.

6. The compound according to claim 1, wherein $R_7$ is a hydrogen atom, a methoxy radical; a methylthio radical, a —$NR_{7a}R_{7b}$ radical or a radical:

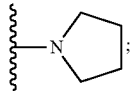

wherein $R_{7a}$ and $R_{7b}$ are as defined in claim 1.

7. The compound according to claim 1, wherein $R_8$ is a hydrogen atom, a halogen atom or a —$(CH_2)_t$—$NR_{8a}R_{8b}$ radical, wherein $R_{8a}$, $R_{8b}$ and t are as defined in claim 1.

8. The compound according to claim 1, having one of the following formulas:

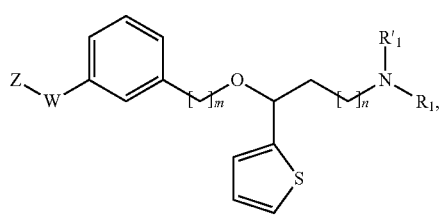

(I$_{1a}$)

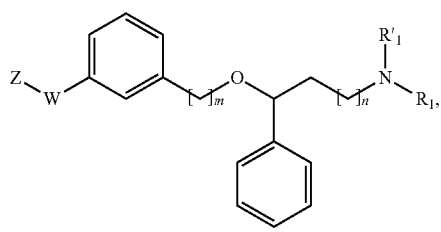

(I$_{1b}$)

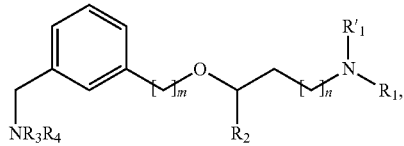

(I$_{2a}$)

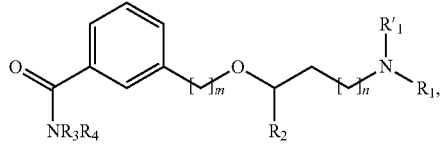

(I$_{2b}$)

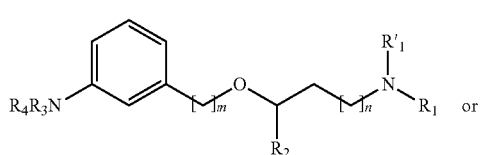

(I$_{2c}$) or

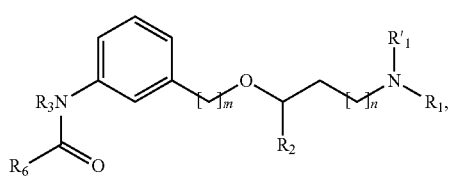

(I$_{2ca}$)

wherein $R_1$, $R'_1$, $R_2$, $R_3$, $R_4$, $R_6$, W, Z, m and n are as defined in claim 1.

9. The compound according to claim 1, which is selected from the group consisting of:
  3-(3-((Benzyl(ethyl)amino)methyl)phenoxy)-N-methyl-3-(thiophen-2-yl)propan-1-amine,
  3-(3-((Benzylamino)methyl)phenoxy)-N-methyl-3-(thiophen-2-yl)propan-1-amine,
  N-methyl-3-(3-((methylamino)methyl)phenoxy)-3-(thiophen-2-yl)propan-1-amine,
  3-(3-((Dimethylamino)methyl)phenoxy)-N-methyl-3-(thiophen-2-yl)propan-1-amine,
  3-(3-((Ethylamino)methyl)phenoxy)-N-methyl-3-(thiophen-2-yl)propan-1-amine,
  3-(3-((Benzyl(methyl)amino)methyl)phenoxy)-N-methyl-3-(thiophen-2-yl)propan-1-amine,
  3-(3-(Methylamino)-1-(thiophen-2-yl)propoxy)-N-(pyridin-2-ylmethyl)benzamide,
  3-(3-(Methylamino)-1-(thiophen-2-yl)propoxy)-N-(pyridin-3-yl)benzamide,
  N-(3-(5-methyl-1,3,4-oxadiazol-2-yl)phenyl)-3-(3-(methylamino)-1-(thiophen-2-yl)propoxy)benzamide,
  N-benzyl-3-(3-(methylamino)-1-(thiophen-2-yl)propoxy)benzamide,
  N-(2-((dimethylamino)methyl)phenyl)-3-(3-(methylamino)-1-(thiophen-2-yl)propoxy)benzamide,
  N-(2-(dimethylamino)phenyl)-3-(3-(methylamino)-1-(thiophen-2-yl)propoxy)benzamide,
  3-(3-(Methylamino)-1-phenylpropoxy)-N-phenylbenzamide,
  N-(3-(5-methyl-1,3,4-oxadiazol-2-yl)phenyl)-3-(3-(methylamino)-1-phenylpropoxy)benzamide,
  3-(3-(Methylamino)-1-phenylpropoxy)-N-(pyridin-3-yl)benzamide,
  N-methyl-3-(3-(methylamino)-1-phenylpropoxy)benzamide, N-benzyl-3-(3-(methylamino)-1-phenylpropoxy)benzamide,
3-(3-(Methylamino)-1-phenylpropoxy)-N-(pyridin-2-ylmethyl)benzamide,
N-ethyl-3-(3-(methylamino)-1-phenylpropoxy)benzamide,
3-(3-(Methylamino)-1-phenylpropoxy)-N-(2-(methylamino)ethyl)benzamide,
N-(6-(ethylamino)pyridin-3-yl)-3-(3-(methylamino)-1-phenylpropoxy)benzamide,
3-(3-(Methylamino)-1-phenylpropoxy)-N-(1-methylpiperidin-4-yl)benzamide,
N-methyl-N-(3-(3-(methylamino)-1-phenylpropoxy)phenyl)benzamide,
N-methyl-N-(3-(3-(methylamino)-1-phenylpropoxy)phenyl)acetamide,
N-methyl-N-(3-(3-(methylamino)-1-phenylpropoxy)phenyl)butyramide,
N-methyl-N-(3-(3-(methylamino)-1-phenylpropoxy)phenyl)nicotinamide,
3-(Aminomethyl)-N-methyl-N-(3-(3-(methylamino)-1-phenylpropoxy)phenyl)benzamide,
4-Amino-N-methyl-N-(3-(3-(methylamino)-1-phenylpropoxy)phenyl)butanamide,
2-(Ethylamino)-N-methyl-N-(3-(3-(methylamino)-1-phenylpropoxy)phenyl)-4-(pyrrolidin-1-yl)pyrimidine-5-carboxamide,
2-(Ethylamino)-N-methyl-N-(3-(3-(methylamino)-1-(thiophen-2-yl)propoxy)phenyl)-4-(pyrrolidin-1-yl)pyrimidine-5-carboxamide,
N-methyl-N-(3-((3-(methylamino)-1-phenylpropoxy)methyl)phenyl)benzamide,
N-methyl-N-(3-((3-(methylamino)-1-phenylpropoxy)methyl)phenyl)nicotinamide,
2-Methoxy-N-methyl-N-(3-((3-(methylamino)-1-phenylpropoxy)methyl)phenyl)pyrimidine-5-carboxamide,
N-methyl-N-(3-((3-(methylamino)-1-phenylpropoxy)methyl)phenyl)pyrimidine-5-carboxamide,
N-methyl-N-(3-((3-(methylamino)-1-phenylpropoxy)methyl)phenyl)-2-(methylthio)pyrimidine-5-carboxamide,
N-methyl-N-(3-((3-(methylamino)-1-phenylpropoxy)methyl)phenyl)picolinamide,
2-(Ethylamino)-N-methyl-N-(3-((3-(methylamino)-1-phenylpropoxy)methyl)phenyl)-4-(pyrrolidin-1-yl)pyrimidine-5-carboxamide,
2-(Ethylamino)-N-methyl-N-(3-((3-(methylamino)-1-(thiophen-2-yl)propoxy)methyl)phenyl)-4-(pyrrolidin-1-yl)pyrimidine-5-carboxamide,
N-(3-((3-(methylamino)-1-phenylpropoxy)methyl)phenyl)benzamide,
N-(3-((3-(methylamino)-1-phenylpropoxy)methyl)phenyl)nicotinamide,
2-Methoxy-N-(3-((3-(methylamino)-1-phenylpropoxy)methyl)phenyl)pyrimidine-5-carboxamide,
N-(3-((3-(methylamino)-1-phenylpropoxy)methyl)phenyl)pyrimidine-5-carboxamide,
N-(3-((3-(methylamino)-1-phenylpropoxy)methyl)phenyl)picolinamide,
N-(3-((3-(methylamino)-1-phenylpropoxy)methyl)phenyl)-2-(methylthio)pyrimidine-5-carboxamide,
2-(Ethylamino)-N-(3-((3-(methylamino)-1-phenylpropoxy)methyl)phenyl)-4-(pyrrolidin-1-yl)pyrimidine-5-carboxamide,
N-(3-((3-(methylamino)-1-(thiophen-2-yl)propoxy)methyl)phenyl)benzamide,
2-(Dimethylamino)-N-(3-((3-(methylamino)-1-(thiophen-2-yl)propoxy)methyl)phenyl)benzamide,
2-Fluoro-N-(3-((3-(methylamino)-1-(thiophen-2-yl)propoxy)methyl)phenyl)benzamide,
2-(Ethylamino)-N-(3-((3-(methylamino)-1-(thiophen-2-yl)propoxy)methyl)phenyl)-4-(pyrrolidin-1-yl)pyrimidine-5-carboxamide,
2-(Ethylamino)-N-(3-(3-(methylamino)-1-phenylpropoxy)phenyl)-4-(pyrrolidin-1-yl)pyrimidine-5-carboxamide,
2-(Ethylamino)-N-(3-(3-(methylamino)-1-(thiophen-2-yl)propoxy)phenyl)-4-(pyrrolidin-1-yl)pyrimidine-5-carboxamide,
N-benzyl-3-((3-(methylamino)-1-phenylpropoxy)methyl)aniline,
3-((3-(Methylamino)-1-phenylpropoxy)methyl)-N-(pyrimidin-5-ylmethyl)aniline,
N-(3-((3-(dimethylamino)-1-(thiophen-2-yl)propoxy)methyl)phenyl) benzamide,
2-(Dimethylamino)-N-(3-((3-(dimethylamino)-1-(thiophen-2-yl)propoxy)methyl)phenyl)benzamide,
N-ethyl-N-(3-(3-(methylamino)-1-(thiophen-2-yl)propoxy)benzyl) benzamide,
N-benzyl-N-(3-((3-(methylamino)-1-phenylpropoxy)methyl)phenyl) acetamide,
3-((3-(Methylamino)-1-phenylpropoxy)methyl)-N-phenylaniline,
N-(3-((3-(methylamino)-1-phenylpropoxy)methyl)phenyl)pyrimidin-2-amine,
2-(Ethylamino)-N-methyl-N-(3-(3-(methylamino)-1-phenylpropoxy) phenyl)pyrimidine-5-carboxamide,
N-(3-((3-(methylamino)-1-phenylpropoxy)methyl)phenyl)-N-phenylacetamide,
N-methyl-N-(3-(3-(methylamino)-1-(thiophen-2-yl)propoxy) phenyl)acetamide,
N-methyl-N-(3-(3-(methylamino)-1-(thiophen-2-yl)propoxy)phenyl)benzamide,
N-methyl-N-(3-(3-(methylamino)-1-(thiophen-2-yl)propoxy)phenyl)butyramide,
N-methyl-N-(3-(3-(methylamino)-1-(thiophen-2-yl)propoxy)phenyl)nicotinamide,
N-(3-(3-(methylamino)-1-(thiophen-2-yl)propoxy)phenyl)benzamide,
N-methyl-N-(3-(3-(methylamino)-1-(thiophen-2-yl)propoxy)phenyl)benzamide,
N-methyl-N-(3-(3-(methylamino)-1-phenylpropoxy)phenyl)nicotinamide and
N-methyl-N-(3-(3-(methylamino)-1-phenylpropoxy)phenyl)benzamide;
or a pharmaceutically acceptable salt, isomer or solvate thereof.

10. The compound according to claim 1, having one of the following formulas:

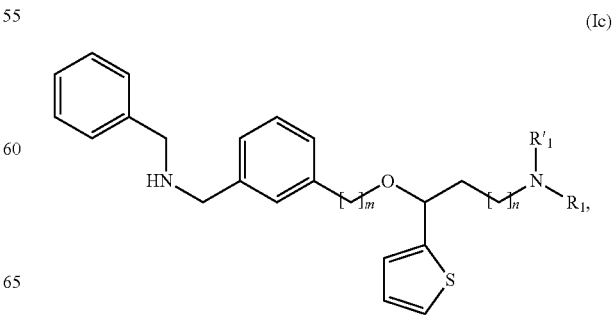

(Ic)

-continued

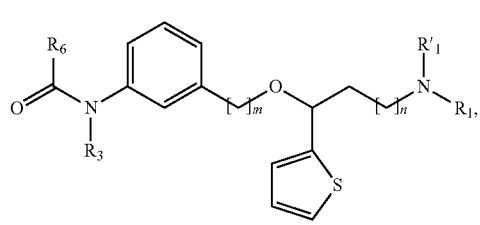 (Id)

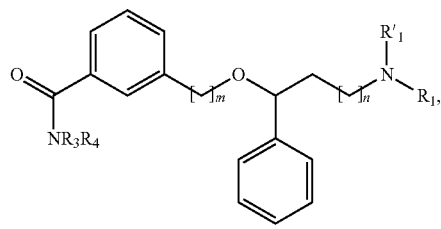 (Ie)

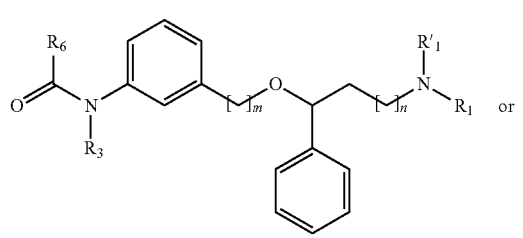 (If)

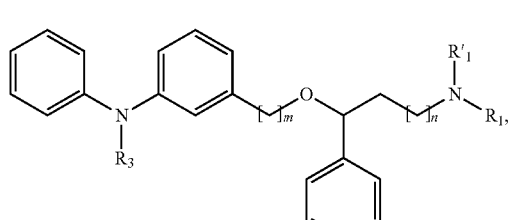 (Ig)

wherein $R_1$, $R'_1$, $R_3$, $R_4$, $R_6$, W, Z, m and n are as defined in claim 1.

11. The compound according to claim 9, which is selected from the group consisting of:
- 3-(3-((Benzylamino)methyl)phenoxy)-N-methyl-3-(thiophen-2-yl)propan-1-amine,
- 3-(3-((Benzyl(methyl)amino)methyl)phenoxy)-N-methyl-3-(thiophen-2-yl)propan-1-amine,
- 3-(3-(Methylamino)-1-phenylpropoxy)-N-phenylbenzamide,
- N-(3-(5-methyl-1,3,4-oxadiazol-2-yl)phenyl)-3-(3-(methylamino)-1-phenylpropoxy)benzamide,
- 3-(3-(Methylamino)-1-phenylpropoxy)-N-(pyridin-3-yl)benzamide,
- N-benzyl-3-(3-(methylamino)-1-phenylpropoxy)benzamide,
- 3-(3-(Methylamino)-1-phenylpropoxy)-N-(pyridin-2-ylmethyl)benzamide,
- 3-(3-(Methylamino)-1-phenylpropoxy)-N-(2-(methylamino)ethyl)benzamide,
- 3-(3-(Methylamino)-1-phenylpropoxy)-N-(1-methylpiperidin-4-yl)benzamide,
- 3-(Aminomethyl)-N-methyl-N-(3-(3-(methylamino)-1-phenylpropoxy)phenyl)benzamide,
- 4-Amino-N-methyl-N-(3-(3-(methylamino)-1-phenylpropoxy)phenyl)butanamide,
- 2-(Ethylamino)-N-methyl-N-(3-((3-(methylamino)-1-(thiophen-2-yl)propoxy)methyl)phenyl)-4-(pyrrolidin-1-yl)pyrimidine-5-carboxamide,
- N-(3-((3-(methylamino)-1-phenylpropoxy)methyl)phenyl)benzamide,
- 2-methoxy-N-(3-((3-(methylamino)-1-phenylpropoxy)methyl)phenyl)pyrimidine-5-carboxamide,
- N-(3-((3-(methylamino)-1-phenylpropoxy)methyl)phenyl)picolinamide,
- N-(3-((3-(methylamino)-1-(thiophen-2-yl)propoxy)methyl)phenyl)benzamide,
- 2-Fluoro-N-(3-((3-(methylamino)-1-(thiophen-2-yl)propoxy)methyl)phenyl)benzamide,
- 2-(Ethylamino)-N-(3-(3-(methylamino)-1-phenylpropoxy)phenyl)-4-(pyrrolidin-1-yl)pyrimidine-5-carboxamide and
- 3-((3-(Methylamino)-1-phenylpropoxy)methyl)-N-phenylaniline;

or a pharmaceutically acceptable salt, isomer or solvate thereof.

12. A compound selected from the group consisting of:
[70] 3-(4-((Benzyl(methyl)amino)methyl)-3-fluorophenoxy)-N-methyl-3-(thiophen-2-yl)propan-1-amine and
[71] 3-(4-((Benzylamino)methyl)-3-fluorophenoxy)-N-methyl-3-(thiophen-2-yl)propan-1-amine;

or a pharmaceutically acceptable salt, isomer or solvate thereof.

13. A process for the preparation of a compound of general formula (Ia):

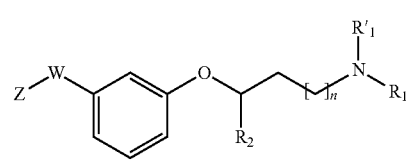 (Ia)

comprising:

a) reaction of a compound of formula (IIa):

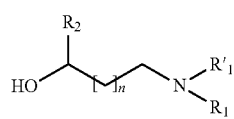 (IIa)

with a compound of formula (IIIa) or (IIIb):

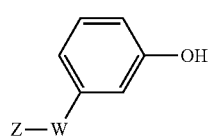 (IIIa)

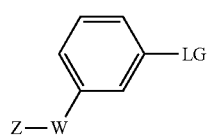 (IIIb)

or;

b) reaction of a compound of formula (IV-LG):

(IV-LG)

with a compound of formula (VI):

         (VI), wherein $R_1$, $R'_1$, $R_2$, W, Z and n are as defined in claim 1 for the compound of formula (I), and LG represents a leaving group.

14. A process for the preparation of a compound of general formula (Ib):

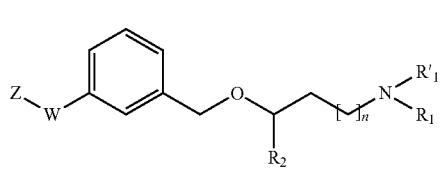         (Ib)

comprising:
a) reaction of a compound of formula (IIa):

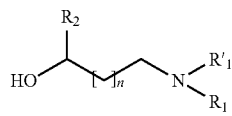         (IIa)

with a compound of formula (IIIc):

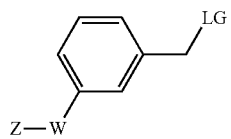         (IIIc)

or;
b) deprotection of a compound of formula (V-P):

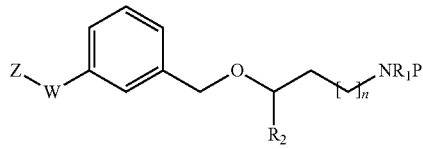         (V-P)

wherein $R_1$, $R'_1$, $R_2$, W, Z and n are as defined in claim 1 for the compound of formula (I), LG represents a leaving group and P represents a protecting group.

15. A process for the preparation of the compound of general formula (I) according to claim 1:

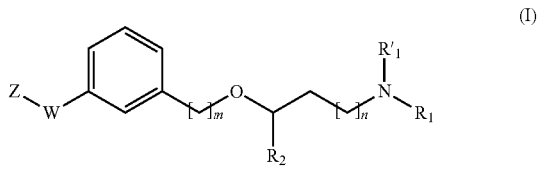         (I)

starting from a compound of formula (VII):

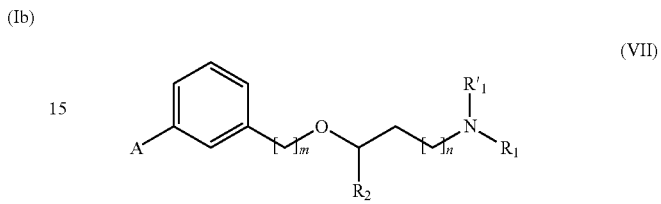         (VII)

wherein $R_1$, $R'_1$, $R_2$, W, Z, m and n are as defined in claim 1, and wherein A represents an aldehyde, a carboxylic acid, a nitro group or a leaving group or —$(CH_2)_p$-LG, wherein LG represents a leaving group, and p is 1 or 2, and wherein the reaction is dependent on the nature of A and W, resulting in that the reaction comprises:
  a reductive amination reaction in the presence of a reductive agent when A is an aldehyde and W is —$(CH_2)_p$—;
  reaction in the presence of a carboxilic acid activating reagent when A is a carboxilic acid and W is a —C(O)— group;
  a coupling reaction in the presence of a metal catalyst when A is a leaving group and W is a bond;
  a reduction reaction when A is a nitro group and W is a bond; or
  a reaction in the presence of a base when A is —$(CH_2)_p$-LG group and W is a —$(CH_2)_p$— group.

16. A method for the treatment of pain in a subject in need thereof, comprising administration of an effective amount of the compound according to claim 1.

17. The method according to claim 16, where the pain is selected from medium to severe pain, visceral pain, chronic pain, cancer pain, migraine, inflammatory pain, acute pain or neuropathic pain or other pain conditions involving allodynia and/or hyperalgesia, depression, anxiety and attention-deficit-/hyperactivity disorder.

18. A pharmaceutical composition comprising the compound according to claim 1, or a pharmaceutically acceptable salt, isomer, prodrug or solvate thereof, and at least a pharmaceutically acceptable carrier, additive, adjuvant or vehicle.

19. The method according to claim 17, where the pain is medium to severe pain.

20. The method according to claim 17, where the pain is acute pain.

21. The method according to claim 17, where the pain is chronic pain.

* * * * *